（12） United States Patent
Wagner et al.

(10) Patent No.: US 12,076,323 B2
(45) Date of Patent: *Sep. 3, 2024

(54) TREATMENT OF HAIR LOSS DISORDERS WITH DEUTERATED JAK INHIBITORS

(71) Applicant: Sun Pharmaceutical Industries, Inc., Princeton, NJ (US)

(72) Inventors: Amanda T. Wagner, Watertown, MA (US); James V. Cassella, Essex, CT (US); Philip B. Graham, Boston, MA (US); Virginia Braman, Winchester, MA (US); Vinita Uttamsingh, Chestnut Hill, MA (US); Jana Von Hehn, Newton, MA (US); Colleen E. Hamilton, Carlisle, MA (US)

(73) Assignee: Sun Pharmaceuticals Industries, Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/704,402

(22) Filed: Dec. 5, 2019

(65) Prior Publication Data

US 2020/0222408 A1     Jul. 16, 2020

Related U.S. Application Data

(63) Continuation of application No. 16/098,338, filed as application No. PCT/US2017/031142 on May 4, 2017, now Pat. No. 10,561,659.

(60) Provisional application No. 62/492,758, filed on May 1, 2017, provisional application No. 62/466,358, filed on Mar. 2, 2017, provisional application No. 62/434,404, filed on Dec. 14, 2016, provisional application No. 62/419,237, filed on Nov. 8, 2016, provisional application No. 62/418,774, filed on Nov. 7, 2016, provisional application No. 62/338,869, filed on May 19, 2016, provisional application No. 62/331,827, filed on May 4, 2016.

(51) Int. Cl.
*A61K 31/519* (2006.01)
*A61K 9/00* (2006.01)
*A61K 9/20* (2006.01)
*A61P 17/14* (2006.01)

(52) U.S. Cl.
CPC .......... *A61K 31/519* (2013.01); *A61K 9/0053* (2013.01); *A61K 9/2009* (2013.01); *A61K 9/2013* (2013.01); *A61K 9/2027* (2013.01); *A61K 9/2054* (2013.01); *A61P 17/14* (2018.01)

(58) Field of Classification Search
CPC ...... A61K 31/519; C07D 487/04; A61P 17/14
USPC ...................... 514/265.1; 544/280
See application file for complete search history.

(56) References Cited

U.S. PATENT DOCUMENTS

| | | | |
|---|---|---|---|
| 7,598,257 B2 | 10/2009 | Rodgers et al. | |
| 9,198,911 B2 | 12/2015 | Christiano et al. | |
| 9,249,149 B2* | 2/2016 | Silverman .......... | A61K 31/7068 |
| 9,662,335 B2 | 5/2017 | Rodgers et al. | |
| 10,265,258 B2 | 4/2019 | Christiano et al. | |
| 10,561,659 B2 | 2/2020 | Wagner et al. | |
| 2008/0312258 A1 | 12/2008 | Rodgers et al. | |
| 2014/0135350 A1 | 5/2014 | Ni et al. | |
| 2015/0239896 A1 | 8/2015 | Silverman et al. | |

FOREIGN PATENT DOCUMENTS

| | | | |
|---|---|---|---|
| CN | 103370076 A | 10/2013 | |
| CN | 104507946 A | 4/2015 | |
| CN | 104725380 A | 6/2015 | |
| JP | 2014/500249 A | 1/2014 | |
| JP | 2015117185 A | 6/2015 | |
| JP | 2015/537030 A | 12/2015 | |
| WO | WO-2012061537 A2 * | 5/2012 | ............ A61K 48/00 |
| WO | WO-2013/149194 A1 | 10/2013 | |

(Continued)

OTHER PUBLICATIONS

Notice of Allowance for U.S. Appl. No. 16/098,338, "Treatment of Hair Loss Disorders with Deuterated JAK Inhibitors," dated Nov. 27, 2019.

(Continued)

*Primary Examiner* — Jeffrey H Murray
(74) *Attorney, Agent, or Firm* — MEDLER FERRO WOODHOUSE & MILLS PLLC

(57) ABSTRACT

Disclosed is a method of treating in a subject hair loss disorders that are beneficially treated by administering a JAK1 and/or JAK2 inhibitor. The method comprises administering to the subject an amount in the range of about 4 mg to about 50 mg of Compound (I):

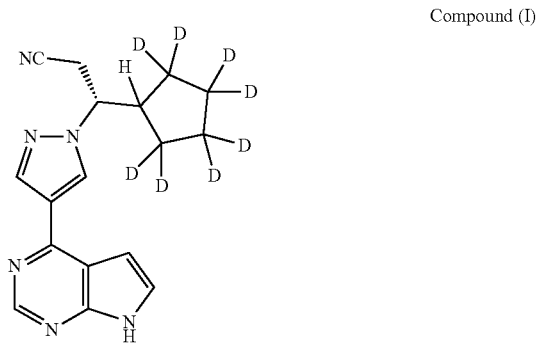

Compound (I)

or a pharmaceutically acceptable salt thereof. This invention also provides compositions comprising Compound (I) and the use of such compositions in the described methods.

29 Claims, 5 Drawing Sheets

(56) References Cited

FOREIGN PATENT DOCUMENTS

| WO | WO-2014/078486 A1 | 5/2014 |
|---|---|---|
| WO | WO-2015/120110 A2 | 8/2015 |

OTHER PUBLICATIONS

Buteau, "Deuterated Drugs: Unexpectedly Nonobvious?," *Journal of High Technology Law, Suffolk University Law School*, XI: 22-74 (2009).
Concert Pharmaceuticals Inc. Precision Deuterium Chemistry Backgrounder—Non-Confidential, 2007, pp. 1-6.
Craiglow et al., "Killing Two Birds with One Stone: Oral Tofacitinib Reverses Alopecia Universalis in a Patient with Plaque Psoriasis," J Investig Dermatol 134:2988-2990 (2014).
Craiglow et al., "Topical Ruxolitinib for the Treatment of Alopecia Universalis," JAMA Dermatol 152(4):490-491 (2016).
Crispin et al., "Safety and efficacy of the JAK inhibitor tofacitinib citrate in patients with alopecia areata," JCI Insight 1(15):1-10 (Sep. 22, 2016).
CTP-543 Phase 2 Results in Patients with Moderate-to-Severe Alopecia Areata. Concert Pharmaceuticals Inc. Presentation on Sep. 3, 2019.
Delamere et al., "Interventions for alopecia areata (Review)," Cochrane Database of Sys Revs 2 (2008).
Final Written Decision (Apr. 8, 2019) in IPR 2017-01256 (U.S. Pat. No. 9,249,149).
Harris et al., "Rapid skin repigmentation on oral ruxolitinib in a patient with coexistent vitiligo and alopecia areata," J Amer Acad Dermatol 74(2):370-371 (Feb. 2016).
Hordinsky, Treatment of alopecia areata: "What is new on the horizon?" Dermatol Therap 24:364-368 (2011).
Huang et al., "Autoimmune, Atopic, and Mental Health Comorbid Conditions Associated With Alopecia Areata in the United States," JAMA Dermatol 131(7):789-794 (2013).
Hunt et al., "The psychological impact of alopecia," BMJ 331:951-953 (2005).
International Search Report and Written Opinion for International Application No. PCT/US2017/031142 dated Jul. 20, 2017.
Jabbari et al., "Reversal of Alopecia Areata Following Treatment With the JAK1/2 Inhibitor Baricitinib," EBioMed 2:351-355 (2015).
Jakafi™ (ruxolitinib) Prescribing Information (2011).
Liu et al., "Tofacitinib for the treatment of severe alopecia areata and variants: A study of 90 patients," J Am Acad Dermatol 76(1):22-28 (2017); published online Nov. 2, 2016, http://dx.doi.org/10.1016/j.jaad.2016.09.007.
Mackay-Wiggan et al., "Oral ruxolitinib induces hair regrowth in patients with moderate-to-severe alopecia areata," J. Clin. Invest. Insight (Sep. 22, 2016).
Notice of Appeal from the Final Written Decision in IPR 2017-01256 to the United States Court of Appeal for the Federal Circuit (Jun. 7, 2019).
Pieri et al., "Ruxolitinib-induced reversal of alopecia universalis in a patient with essential thrombocythemia," AJH 90(1):82-83 (2015).
Pilot Study to Evaluate the Efficacy of Ruxolitinib in Alopecia Areata, ClinicalTrials.gov Identifier: NCT01950780 (2013) <https://clinicaltrials.gov/ct2/show/NCT01950780?term=NCT01950780&rank=1> [Date Accessed: Sep. 27, 2018].
Press Release "Concert Pharmaceuticals Announces CTP-543 Positive Top-Line Phase 1 Results," Dec. 14, 2016.
Press Release "Concert Pharmaceuticals Reports Positive CTP-543 Results from Phase 2 Alopecia Areata Trial," Sep. 3, 2019.
Shi et al., "The Effect of CYP3A4 Inhibition or Induction on the Pharmacokinetics and Pharmacodynamics of Orally Administered Ruxolitinib (INCB018424 Phosphate) in Healthy Volunteers," J Clin Pharmacol 52:809-818 (2012).
Shi et al., "The pharmacokinetics, pharmacodynamics and safety of orally dosed INC18424 phosphate in healthy volunteers," J. Clin. Pharmacol, 51:1644-165 (2011).
Shilling et al., "Metabolism, Excretion, and Pharmacokinetics of [14C]INCB018424, A Selective Janus Tyrosine Kinase 1/2 Inhibitor, in Humans," *Drug Metabolism and Disposition*, 38(11):2023-2031 (2010).
Supplementary European Search Report for EP application No. EP 17793380 dated Nov. 15, 2019.
The Voice of the Patient: A series of reports from the U.S. Food and Drug Administration's (FDA's) Patient-Focused Drug Development Initiative, Alopecia Areata (2018).
Tung, "The Development of Deuterium-Containing Drugs," Inn Pharma Technol 32:24-28 (2010).
Vandiver et al., "Two cases of alopecia areata treated with ruxolitinib: a discussion of ideal dosing and laboratory monitoring," Int J Dermatol 56:833-835 (2017).
Xing et al., "Alopecia areata is driven by cytotoxic T lymphocytes and is reversed by JAK inhibition," Nature Med. 20: 1043-49 (2014).
PGR2021-00006 EX1004: Jakafi® (ruxolitinib) Prescribing Information, Physicians' Desk Reference 1281-1287 (69$^{th}$ ed. 2015).
PGR2021-00006 EX1009: Declaration of Dr. Jerry Shapiro, M.D.
PGR2021-00006 EX1011: Amanda Yarnell, *Heavy-Hydrogen Drugs Turn Heads, Again*, Chem. Eng. News 87(25):36-39 (2009).
PGR2021-00006 EX1013: Lynn Petukhova & Angela M. Christiano, *Functional Interpretation of Genome-Wide Association Study Evidence in Alopecia Areata*, J. Invest. Dermatol. 136(1):314-317 (2016).
PGR2021-00006 EX1014: Sherrie J. Divito & Thomas S. Kupper, *Inhibiting Janus kinases to treat alopecia areata*, Nat. Med. 20:989-990 (2014).
PGR2021-00006 EX1016: Sivan Harel et al., *Pharmacologic inhibition of JAK-STAT signaling promotes hair growth*, Sci. Adv. 1(9) (2015).
PGR2021-00006 EX1017: F. Silvestri et al., *Ruxolitinib for the treatment of alopecia areata*, Ital. J. Med. 10(Suppl. 2): 108 (2016).
PGR2021-00006 EX1019: Nature Medicine Journal 2019 Metrics Website, https://www.nature.com/nature-research/about/journal-metrics (last visited Oct. 28, 2020).
PGR2021-00006 EX1020: John J. O'Shea et al., *The JAK-STAT Pathway: Impact on Human Disease and Therapeutic Intervention*, Annu. Rev. Med. 66:311-328 (2015).
PGR2021-00006 EX1022: Naseeha Islam et al., *The autoimmune basis of alopecia areata: A comprehensive review*, Autoimmun. Rev. 14(2):81-89 (2015).
PGR2021-00006 EX1023: *Incyte Corp. v. Concert Pharmaceuticals, Inc.*, IPR2017-01256, Paper 29 (PTAB Jul. 2, 2018).
PGR2021-00006 EX1024: Affidavit of Elaine Rosselle (Feb. 28, 2020).
PGR2021-00006 EX1025: Sittiporn Bencharit & Michael G. Quon, *Metabolic Acidosis Associated with Propofol Use*, Proceedings of UCLA Healthcare 19 (2015).
PGR2021-00006 EX1026: Lynn Petukhova et al., *Genome-wide association study in alopecia areata implicates both innate and adaptive immunity*, Nature 466(7302): 113-117 (2010).
PGR2021-00006 EX1028: Craiglow 2016 copyright record.
PGR2021-00006 EX1029: Harris 2016 copyright record.
PGR2021-00006 EX1030: Pieri 2015 copyright record.
PGR2021-00006 EX1033: Thomas G. Gant, *Using Deuterium in Drug Discovery: Leaving the Label in the Drug*, J. Med. Chem. 57(9):3595-3611 (2014).
PGR2021-00006 EX1035: *Imidazo[1,2-a]pyrazine Core: Fluorine and Deuterium Incorporation Improve Oral Absorption and Exposure*, J. Med. Chem. 54:201-210 (2011).
PGR2021-00006 EX1036: Liming Shao et al., *Derivatives of tramadol for increased duration of effect*, BioOrg. Med. Chem. Lett. 16(3):691-694 (2006).
PGR2021-00006 EX1037: Cath O'Driscoll, *Heavyweight drugs*, Chemistry & Industry 24-26 (2009).
PGR2021-00006 EX1038: Allan B. Foster, *Deuterium Isotope Effects in the Metabolism of Drugs and Xenobiotics: Implications for Drug Design*, Adv. Drug Res. 14:1-40 (1985).
PGR2021-00006 EX1039: Julie F. Liu et al., *CTP-354: A novel deuterated subtype-selective GABA(A) modulator for treatment of neuropathic pain, spasticity and anxiety disorders* (2012).

(56) References Cited

OTHER PUBLICATIONS

PGR2021-00006 EX1040: Scott L. Harbeson et al., *Pharmacokinetic Studies of Deuterated Isotopologs of Ivacaftor in Preclinical Models and Healthy Volunteers* (2015).
PGR2021-00006 EX1041: Asher Mullard, *Deuterated drugs draw heavier backing*, Nat. Rev. Drug Discov. 15:219-221 (2016).
PGR2021-00006 EX1042: Zacks Small-Cap Research, Auspex Pharmaceuticals Inc. (2014).
PGR2021-00006 EX1043: *Drug Repositioning Brining New Life to Shelved Assets and Existing Drugs* (Michael J. Barratt & Donald E. Frail eds., 2012).
PGR2021-00006 EX1044: Rowan A. Stringer et al., *Application of a Deuterium Replacement Strategy to Modulate the Pharmacokinetics of 7- (3,5-dimethyl-1H-1,2,4-triazol-1-yl)-3-(4-methoxy-2-methylphenyl)-2, 6-dimethylpyrazolo[5, 1-b]oxazole, a Novel $CRF_1$ Antagonist*, Drug Metab. Dispos. 42:954-962 (2014).
PGR2021-00006 EX1047: File History of U.S. Pat. No. 10,561,659.
PGR2021-00006 EX1049: Julian Mackay-Wiggan et al., *Oral ruxolitinib induces hair regrowth in patients with moderate-to-severe alopecia areata*, J. Clin. Invest. Insight 1(15) (2016).
PGR2021-00006 EX1050: Brittany G. Craiglow & Brett A. King, *Killing Two Birds with One Stone: Oral Tofacitinib Reverses Alopecia Universalis in a Patient with Plaque Psoriasis*, J. Invest. Dermatol. 134(12):2988-2990 (2014).
PGR2021-00006 EX1051: Alla Katsnelson, *Heavy drugs draw heavy interest from pharma backers*, Nature Medicine 19(6):656 (2013).
PGR2021-00006 EX1052: Vinita Uttamsingh et al., *Altering Metabolic Profiles of Drugs by Precision Deuteration: Reducing Mechanism-Based Inhibition of CYP2D6 by Paroxetine*, J. Pharmacol. Exp. Ther. 354:43-54 (2015).
PGR2021-00006 EX1053: Ruixue Xu et al., *Design, synthesis and biological evaluation of deuterated nintedanib for improving pharmacokinetic properties*, J. Label. Compd. Radiopharm. 58:308-312 (2015).
PGR2021-00006 EX1054: Virginia Braman et al., *A Randomized Phase I Evaluation of CTP-499, a Novel Deuterium-Containing Drug Candidate for Diabetic Nephropathy*, Clin. Pharmacol. Drug Dev. 2(1):53-66 (2013).
PGR2021-00006 EX1056: R. Scott Obach, *Prediction Of Human Clearance Of Twenty-Nine Drugs From Hepatic Microsomal Intrinsic Clearance Data: An Examination Of In Vitro Half-Life Approach And Nonspecific Binding To Microsomes*, Drug Metab. Dispos. 27(11):1350-1359 (1999).
PGR2021-00006 EX1057: Gerald T. Miwa & Anthony Y. H. Lu, *Kinetic Isotope Effects and Metabolic Switching' in Cytochrome P450-Catalyzed Reactions*, BioEssays 7(5):215-219 (1987).
PGR2021-00006 EX1058: Raman Sharma et al., *Deuterium Isotope Effects on Drug Pharmacokinetics. I. System-Dependent Effects of Specific Deuteration with Aldehyde Oxidase Cleared Drugs*, Drug Metab. Dispos. 40(3):625-634 (2012).
PGR2021-00006 EX1061: Adam J. Morgan et al., *Design and synthesis of deuterated boceprevir analogs with enhanced pharmacokinetic properties*, J. Label. Compd. Radiopharm. 54(9):613-624 (2011).
PGR2021-00006 EX1062: Marty E. Sawaya & Jerry Shapiro, *Alopecia: Unapproved Treatments or Indications*, Clinics in Dermatology 18:177-186 (2000).
PGR2021-00006 EX1063: Doryx® Prescribing Information (Jun. 2008).
PGR2021-00006 EX1064: Loniten® Prescribing Information, Physicians' Desk Reference 2928-2929 ($49^{th}$ ed. 1995).
PGR2021-00006 EX1065: Aldactone® Prescribing Information, Physicians' Desk Reference 2558-2561 ($53^{rd}$ ed. 1999).
PGR2021-00006 EX1066: Xeljanz® Prescribing Information (Dec. 2019).
PGR2021-00006 EX1067: William Abramovits et al., *Tofacitinib citrate alleviates alopecia universalis symptoms in recent case study*, J. Am Acad. Dermatology Suppl. 1:AB175 (2016).

PGR2021-00006 EX1068: A. Jabbari et al., *An open label pilot clinical trial of the JAK inhibitor tofacitinib for alopecia areata* Journal of Investigative Dermatology Abstract 277:S49 (2016).
PGR2021-00006 EX1069: U.S. Food and Drug Administration, *Guidance for Industry: Exposure-Response Relationships—Study Design, Data Analysis, and Regulatory Applications* (2003).
PGR2021-00006 EX1070: L. J. Lesko & A. J. Atkinson, Jr., *Use of Biomarkers and Surrogate Endpoints in Drug Development and Regulatory Decision Making: Criteria, Validation, Strategies*, Annu. Rev. Pharmacol. Toxicol. 41:347-366 (2001).
PGR2021-00006 EX1071: James D. Clark et al., *Discovery and Development of Janus Kinase (JAK) Inhibitors for Inflammatory Diseases*, J. Med. Chem. 57:5023-5038 (2014).
PGR2021-00006 EX1072: Jack G. Shi et al., *The Pharmacokinetics, Pharmacodynamics, and Safety of Baricitinib, an Oral JAK 1/2 Inhibitor, in Healthy Volunteers*, J. Clin. Pharmacol. 54(12):1354-1361 (2014).
PGR2021-00006 EX1073: Edward C. Keystone et al., *Safety and efficacy of baricitinib at 24 weeks in patients with rheumatoid arthritis who have had an inadequate response to methotrexate*, Ann. Rheum. Dis. 74:333-340 (2015).
PGR2021-00006 EX1074: K. A. Papp et al., *A randomized phase 2b trial of baricitinib, an oral Janus kinase (JAK) 1/JAK2 inhibitor, in patients with moderate-to-severe psoriasis*, BR. J. Dermatol. 174(6):1266-1276 (2016).
PGR2021-00006 EX1075: Ronald J. Tallarida & Robert B. Raffa, *The application of drug dose equivalence in the quantitative analysis of receptor occupation and drug combinations*, Pharmacol. Ther. 127(2):165-174 (2010).
PGR2021-00006 EX1076: Ronald J. Tallarida, *Drug Combinations: Tests and Analysis with Isoboles*, Curr. Protoc. Pharmacol. Suppl. 72: 9.19.1-9.19.19 (2016).
PGR2021-00006 EX1077: Bruno G. Reigner & Karen Smith Blesch, *Estimating the starting dose for entry into humans: principles and practice*, Eur. J. Clin. Pharmacol. 57:835-845 (2002).
PGR2021-00006 EX1078: Srdan Verstovsek et al., *A Phase II Study of Ruxolitinib, an Oral JAK1 and JAK2 Inhibitor, in Patients With Advanced Polycythemia Vera Refractory or Intolerant to Hydroxyurea*, Cancer. 120(4):513-520 (2014).
PGR2021-00006 EX1079: Olumiant® Prescribing Information (May 2018).
PGR2021-00006 EX1080: Yury Grabovsky & Ronald J. Tallarida, *Isobolographic Analysis for Combinations of a Full and Partial Agonist: Curved Isoboles*, J. Pharmacol. Exp. Ther. 310(3):981-986 (2004).
PGR2021-00006 EX1081: Jean-Baptiste Telliez, *Janus Kinase Inhibitors*, Compendium of Inflammatory Diseases 787-791 (Michael J. Parnham ed., 2016).
PGR2021-00006 EX1082: U.S. Food and Drug Administration, *Guidance for Industry: Providing Clinical Evidence of Effectiveness for Human Drug and Biological Products* (1998).
PGR2021-00006 EX1083: Srdan Verstovsek et al., *Management of cytopenias in patients with myelofibrosis treated with ruxolitinib and effect of dose modifications on efficacy outcomes*, Oncotargets Ther. 7:13-21 (2014).
PGR2021-00006 EX1084: *Concert Pharmaceuticals Announces $8 Million Milestone from Celgene*, Business Wire (Oct. 8, 2015), https://ir.concertpharma.com/news-releases/news-release- details/concert-pharmaceuticals-announces-8-million-milestone- celgene (last visited Oct. 27, 2020).
PGR2021-00006 EX1085: *Concert Pharmaceuticals Highlights CTP-656 Phase 1 Results at North American Cystic Fibrosis Conference*, (Oct. 8, 2015), https://www.businesswire.com/news/home/20151008005813/en/ Concert-Pharmaceuticals-Highlights-CTP-656-Phase-1-Results- at-North-American-Cystic-Fibrosis-Conference (last visited Oct. 27, 2020).
PGR2021-00006 EX1086: Torun Malmlöf et al., *Deuterium substitutions in the L-DOPA molecule improve its anti-akinetic potency without increasing dyskinesias*, Exp. Neurol. 225(2):408-415 (2010).
PGR2021-00006 EX1087: Edward M. Rudnic & Joseph D. Schwartz, *Oral Solid Dosage Forms*, Remington: The Science and Practice of Pharmacy 858-893 (Alfonso R. Gennaro ed., $20^{th}$ ed. 2000).

(56) References Cited

OTHER PUBLICATIONS

PGR2021-00006 EX1088: Eleanor Higgins et al., *Use of ruxolitinib to successfully treat chronic mucocutaneous candidiasis caused by gain-of-function signal transducer and activator of transcription 1 (STAT1) mutation*, J.Allergy Clin. Immunol. 135(2):551-553.e3 (2015).
PGR2021-00006 EX1089: James Cassella et al., *CTP-543, an Oral JAK Inhibitor, Achieves Primary Endpoint in Phase 2 Randomized, Placebo-Controlled Dose-Ranging Trial in Patients with Moderate-to-Severe Alopecia Areata*, European Academy of Dermatology and Venereology Annual Congress (Oct. 12, 2019).
PGR2021-00006 Petition for Post-Grant Review; Oct. 28, 2020.
PGR2021-00006 EX1018: Luzhou Xing et al., *Alopecia areata is driven by cytotoxic T lymphocytes and is reversed by JAK inhibition*, Nat. Med. 20(9):1043-1049 (2014) (On line version).
PGR2021-00006 EX1032: John E. Harris et al., *Rapid skin repigmentation on oral ruxolitinib in a patient with coexistent vitiligo and alopecia areata (AA)*, J.Am.Acad. Dermatol. 74(2):370-371 (2016) (On line version).
PGR2021-00006 Decision Granting Institution of Post-Grant Review (dated May 12, 2021).
PGR2021-00006 EX 1007: Declaration of Dr. Steven Patterson, Ph.D. (Oct. 28, 2020).
PGR2021-00006 EX 1008: Curriculum Vitae of Dr. Steven Patterson (Oct. 28, 2020).
PGR2021-00006 EX 1009: Declaration of Dr. Jerry Shapiro, M.D. (Oct. 28, 2020).
PGR2021-00006 EX 1010: Curriculum Vitae of Dr. Jerry Shapiro (Oct. 28, 2020).
PGR2021-00006 EX 1015: Daniella M. Schwartz et al., Type I/II cytokines, JAKs, and new strategies for treating autoimmune diseases, Nature Reviews Rheumatology 12(1):25-36 (2016).
PGR2021-00006 EX 1034: Concert Pharmaceuticals, Inc., Precision Deuterium Chemistry Backgrounder (2007).
PGR2021-00006 EX 1045: File history of U.S. Pat. No. 9,249,149 filed on May 8, 2015.
PGR2021-00006 EX 1047: File History of U.S. Pat. No. 10,561,659 filed on Nov. 1, 2018.
PGR2021-00006 EX 1048: Malcolm Rowland & Thomas N. Tozer, Clinical Pharmacokinetics and Pharmacodynamics: Concepts and Applications (4th edition 2011).
PGR2021-00006 EX 1090: File History of U.S. Appl. No. 16/298,795 (filed on Mar. 11, 2019).
PGR2021-00006 EX 1091: Declaration of Raymond O. Cruitt (Oct. 28, 2020).
PGR2021-00006 EX 1093: Declaration of Daniel R. Shelton (Oct. 28, 2020).
PGR2021-00006 EX 1094 : Hearing Transcript of Mar. 10, 2021 (Mar. 17, 2021).
PGR2021-00006 EX 2004: U.S. Priority U.S. Appl. No. 62/331,827 (Filing Date May 4, 2016).
PGR2021-00006 EX 2005: Declaration of Vinita Uttamsingh (dated Feb. 15, 2021).
PGR2021-00006 EX 2007: M.F. McMullin et al., The use of erythropoiesis-stimulating agents with ruxolitinib in patients with myelofibrosis in Comfort-II: an open-label, phase 3 study assessing efficacy and safety of ruxolitinib versus best available therapy in the treatment of myelofibrosis, Exp. Hematol. Oncol. 4:26 (2015).
PGR2021-00006 EX 2009: Declaration of Jerry Shapiro, M.D., IPR2017-01256 (dated Sep. 9, 2018).
PGR2021-00006 EX 2010: Declaration of Alison H. Fitzgerald (dated Feb. 16, 2021).
PGR2021-00006 EX 2011: U.S. Pat. No. 10,561,659—Patent Assignment (Feb. 16, 2021).
PGR2021-00006 EX 2012: U.S. Pat. No. 9,249,149—Patent Assignment (Feb. 16, 2021).
PGR2021-00006 EX 2013: C. Helfand, FDA swats down Pfizer's Xeljanz in plaque psoriasis, Fierce Pharma (Oct. 15, 2015), available online at: https://www.fiercepharma.com/regulatory/fda-swats-down-pfizer-s-xeljanz-plaque-psoriasis.
PGR2021-00006 EX 2014: Concert Pharmaceuticals Inc. Press Release: Concert Pharmaceuticals Receives FDA Breakthrough Therapy Designation for CTP-543 for the Treatment of Alopecia Areata (Jul. 8, 2020), available online at: https://ir.concertpharma.com/news-releases/news-release-details/concert-pharmaceuticals-receives-fda-breakthrough-therapy.
PGR2021-00006 EX 2015 : Steven E. Patterson, Ph.D. Faculty Biography, University of Minnesota—Center for Drug Design, available online at: https://drugdesign.umn.edu/bio/cdd-faculty-staff/steven-patterson (Feb. 16, 2021).
PGR2021-00006 EX 2016: FDA Advisory Committee Recommends the Approval of Baricitinib 2mg, but not 4mg, for the Treatment of Moderately-to-Severely Active Rheumatoid Arthritis available online at: https://investor.lilly.com/news-releases/news-release-details/fda- advisory-committee-recommends-approval-baricitinib-2mg-not (Apr. 24, 2018).
PGR2021-00006 EX 2017 : Plaquenil® (Hydroxychloroquine) Prescribing Information (Rev. Oct. 2006).
PGR2021-00006 EX 2018: Simponi® (Golimumab) Highlights of Prescribing Information (Rev. Jan. 2016).
PGR2021-00006 EX 2019: W. Damsky et al., The emerging role of Janus kinase inhibitors in the treatment of autoimmune and inflammatory diseases, J. Allergy Clin. Immunol. (2020).
PGR2021-00006 EX 2020: Statutory Disclaimer in a Patent Under 37 C.F.R. § 1.321(a), dated Feb. 12, 2021 (U.S. Appl. No. 16/098,338).
PGR2021-00006 EX 2021: Xeljanz® (Tofacitinib) Highlights of Prescribing Information (Rev. Sep. 2020).
PGR2021-00006 EX 2022: S. Banerjee et al., JAK-STAT Signaling as a Target for Inflammatory and Autoimmune Diseases: Current and Future Prospects, Drugs (2017).
PGR2021-00006 EX 2023: Austedo® (Deutetrabenazine) Highlights of Prescribing Information (Rev. Dec. 2020).
PGR2021-00006 EX 2024: Order, *Concert Pharm., Inc.* v. *Incyte Corp.*, No. 19-2011 (Fed. Cir. Jan. 24, 2020).
PGR2021-00006 EX 2025 Mandate, *Concert Pharm., Inc.* v. *Incyte Corp*, No. 19-2011 (Fed. Cir. Apr. 16, 2020).
PGR2021-00006 EX 2026: Concert Pharmaceuticals Inc. Press Release: Concert Pharmaceuticals Reports Positive CTP-543 Results from Phase 2 Alopecia Areata Trial (Sep. 3, 2019), available online at: https://ir.concertpharma.com/node/10986/pdf.
PGR2021-00006 Paper 11: Patent Owner's Preliminary Response (Feb. 16, 2021).
PGR2021-00006 Paper 16: Conduct of the Proceeding Authorizing Reply and Sur-Reply to Patent Owner's Preliminary Response (Mar. 11, 2021).
PGR2021-00006 Paper 17: Petitioner's Reply to Patent Owner's Preliminary Response (Mar. 17, 2021).
PGR2021-00006 Paper 19: Patent Owner's Sur-Reply (Mar. 24, 2021).
PGR2021-0006 Paper 36 Patent Owner's Updated Exhibit List (Aug. 11, 2021).
PGR2021-0006 Paper 37 Patent Owner's Response (Aug. 12, 2021).
PGR2021-0006 Paper 38 Patent Owner's Updated Exhibit List (Aug. 12, 2021).
PGR2021-0006 Paper 44 Petitioner's Reply to Patent Owner's Response (Nov. 12, 2021).
PGR2021-0006 Paper 45 Petitioner's Updated Exhibit List As of Nov. 12, 2021 (Nov. 12, 2021).
PGR2021-00006 EX1112: International Search Report PCT/US2011/064238, completed Feb. 14, 2012.
PGR2021-00006 EX1113: Written Opinion PCT/US2011/064238, completed Feb. 14, 2012.
PGR2021-00006 EX1115: Ep 09 703 515.8, Communication, European Search Opinion, and Supplementary European Search Report (completed Aug. 5, 2011).
PGR2021-00006 EX1120: Declaration of Frederick Peter Guengerich, Ph. D. (Nov. 5, 2021).
PGR2021-00006 EX1121: Curriculum Vitae of Frederick Peter Guengerich, Ph.D. (Nov. 5, 2021).
PGR2021-00006 EX1123: U.S. Patent Application Publication No. 2010/0234388 to Gant et al. (published Sep. 16, 2010).

(56) References Cited

OTHER PUBLICATIONS

PGR2021-00006 EX1124: U.S. Patent Application Publication No. 2012/0252864 to Liu (published Oct. 4, 2012).
PGR2021-00006 EX1125: International Publication No. WO 2007/041630 (published Apr. 12, 2007).
PGR2021-00006 EX1126: Concert Press Release, *Concert Pharmaceuticals Achieves $2 Million Milestone for AVP-786 Under Avanir Pharmaceuticals Collaboration* (Aug. 26, 2014).
PGR2021-00006 EX1127: U.S. Appl. No. 62/492,758 (filed May 1, 2017).
PGR2021-00006 EX1128: Request for Continued Examination and Amendment in Reply to Action of Mar. 5, 2012 dated Sep. 5, 2012, submitted during prosecution of U.S. Appl. No. 13/038,533 (U.S. Pat. No. 8,513,434).
PGR2021-00006 EX1129: U.S. Pat. No. 7,973,049 to Tung (issued Jul. 5, 2011).
PGR2021-00006 EX1130: David J. Greenblat et al., *Sources of variability in ketoconazole inhibition of human cytochrome P450 3A in vitro*, XenoBiotica 40(10):713-720 (2010).
PGR2021-00006 EX1131: David J. Greenblat & Jerold S. Harmatz, *Ritonavir is the best alternative to ketoconazole as an index inhibitor of cytochrome P450-3A in drug- drug interaction studies*, Br. J. Clin. Pharmacol. 80(3):342-350 (2015).
PGR2021-00006 EX1132: Declaration of Vinita Uttamsingh Under 37 CFR § 1.132 dated Apr. 11, 2013, submitted during prosecution of U.S. Appl. No. 13/256,787 (U.S. Pat. No. 8,563,554).
PGR2021-00006 EX1133: Declaration of Vinita Uttamsingh Under 37 CFR § 1.132 dated Oct. 1, 2010, submitted during prosecution of U.S. Appl. No. 12/075,107 (U.S. Pat. No. 7,943,620);.
PGR2021-00006 EX1134: F. Peter Guengerich et al., *Kinetics of cytochrome P450 3A4 inhibition by heterocyclic drugs defines a general sequential multistep binding process*, J. Biol. Chem. 296:1-16 (2021).
PGR2021-00006 EX1135: David J. Greenblatt, *Evidence-Based Choice of Ritonavir as Index CYP3A Inhibitor in Drug-Drug Interaction Studies*, The Journal of Clinical Pharmacology 56(2):152-156 (2016).
PGR2021-00006 EX1136: Don K. Walker et al., *Species Differences in the Disposition of the CCR5 Antagonist, UK-427,857, A New Potential Treatment for HIV*, Drug Metabolish and Disposition 33(4):587-595 (2005).
PGR2021-00006 EX1137: Liming Shao & Michael C. Hewitt, *The Kinetic Isotope Effect In The Search For Deuterated Drugs*, Drug News & Perspectives 23(6):398- 404 (2010).
PGR2021-00006 EX1138: Concert Pharmaceuticals, Inc. SEC 2013 Form 10-K (Mar. 31, 2014).
PGR2021-00006 EX1139: Amanda T. Wagner, *Industry Perspective on Alopecia Areata*, The Journal of Investigative Dermatology Symposium 17:67-69 (2015).
PGR2021-00006 EX1140: Dory Kranz et al., *From Targets to Treatments: Bridging Autoimmune Research to Advance Understanding of Alopecia Areata*, The Journal of Investigative Dermatology Symposium 17:1-5 (2015).
PGR2021-00006 EX1141: Paulo Müller Ramos et al., *Consensus on the treatment of alopecia areata—Brazilian Society of Dermatology*, An. Bras. Dermatol. 95(S1):39-52 (2020).
PGR2021-00006 EX1142: ClinicalTrials.gov identifier NCT01950780, *Pilot Study to Evaluate the Efficacy of Ruxolitinib in Alopecia Areata*, https://www.clinicaltrials.gov/ct2/show/NCT01950780 (last update posted Mar. 7, 2019).
PGR2021-00006 EX1143: Mackay-Wiggan, *Abstracts: Clinical Research (Observations, Pathophysiology & Outcomes)*, Journal of Investigative Dermatology 135:S28-S48 (2015).
PGR2021-00006 EX1144: Wilma F. Bergfeld et al., *Proceedings of the Ninth World Congress for Hair Research* (2015), Journal of Investigative Dermatology Symposium Proceedings 18:S1-S28 (2017).
PGR2021-00006 EX1145: M. J. Harries et al., *Management of alopecia areata*, BMJ 341:c3671 (2010).

PGR2021-00006 EX1146: Srdan Verstovsek et al., *A Double-Blind, Placebo-Controlled Trial of Ruxolitinib for Myelofibrosis*, N. Engl. J. Med. 366(9):799-807 (2012).
PGR2021-00006 EX1147: Claire Harrison et al., *JAK Inhibition with Ruxolitinib versus Best Available Therapy for Myelofibrosis*, N. Engl. J. Med. 366(9):787-798 (2012).
PGR2021-00006 EX1148: William Williams et al., *A Randomized Placebo-Controlled Study of INCB018424, a Selective Janus Kinase 1 & 2 (JAK1&2) Inhibitor in Rheumatoid Arthritis (RA)*, American College of Rheumatology Abstract Supplement S431 (2008).
PGR2021-00006 EX1149: Kerry-Ann L. Dillon, *A Comprehensive Literature Review of JAK Inhibitors in Treatment of Alopecia Areata*, Clinical, Cosmetic and Investigational Dermatology 14:691-714 (2021).
PGR2021-00006 EX1150: Bruce R. Blazar et al., *Adavances in graft-versus-host disease biology and therapy*, Nature Reviews Immunology 12:443-458 (2012).
PGR2021-00006 EX1151: ClinicalTrials.gov identifier NCT02396628, *Ruxolitinib In GvHD (RIG)*, https://www.clinicaltrials.gov/ct2/show/NCT02396628 (last updated posted Dec. 2, 2019).
PGR2021-00006 EX1152: Milène Kennedy Crispin et al., *Safety and efficacy of the JAK inhibitor tofacitinib citrate in patients with alopecia areata*, JCI Insight 1(15):e89776 (2016).
PGR2021-00006 EX1153: S. C. Gordon et al., *Rebound effect associated with JAK inhibitor use in the treatment of alopecia areata*, JEADV 33:e156-e157 (2019).
PGR2021-00006 EX1154: Lilly Press Release, Lilly Receives FDA Breakthrough Therapy Designation for Baricitinib for the Treatment of Alopecia Areata, Mar. 16, 2020, http://www.prnewswire.com/news-releases/lilly-receives-fda- breakthrough-therapy-designationfor-baricitinib-for-the-treatment-of- alopecia-areata-301024437.html.
PGR2021-00006 EX1155: Pfizer Press Release, *Pfizer Receives Breakthrough Therapy Designation From FDA For PF-06651600, An Oral JAK3 Inhibitor, For The Treatment Of Patients With Alopecia Areata*, Sep. 5, 2018, https://www.pfizer.com/news/press-release/press-release-detail/pfizer_receives_breakthrough_therapy_designation_from_fda_for_pf_06651600_an_oral_jak3_inhibitor_for_the_treatment_of_patients_with_alopecia_areata.
PGR2021-00006 EX1156: *Aclaris Press Release, FDA grants Fast Track Designation to Aclaris Therapeutics' Investigational JAK Inhibitor for the treatment of Alopecia Areata*, Jul. 9, 2018, https://aclaristherapeuticsinc.gcs-web.com/news-releases/news-release-details/fda-grants-fast-track-designation-aclaris-therapeutics.
PGR2021-00006 EX1157: R. Zeiser et al., *Ruxolitinib in corticosteroid-refractory graft-versus-host disease after allogeneic stem cell transplantation: a multicenter survey*, Leukemia 29:2062-2068 (2015).
PGR2021-00006 EX1158: Brett King et al., *Efficacy and safety of the oral Janus kinase inhibitor baricitinib in the treatment of adults with alopecia areata*: Phase 2 results from a randomized controlled study, J. Am. Acad. Dermatol. 84(4):847-853 (2021).
PGR2021-00006 EX1159: Declaration of Ronald A. Thisted, Ph. D. (Nov. 10, 2021).
PGR2021-00006 EX1160: Curriculum Vitae of Ronald A. Thisted, Ph D. (Nov. 10, 2021).
PGR2021-00006 EX1161: Declaration of William Damsky, MD, Ph. D. (Nov. 12, 2021).
PGR2021-00006 EX1162: Curriculum Vitae of William Damsky, MD, Ph. D. (Nov. 12, 2021).
PGR2021-00006 EX1163: William J. Taylor & Mark Weatherall, *Editorial: What Are Open-Label Extension Studies For?*, The Journal of Rheumatology 33(4):642- 643 (2006).
PGR2021-00006 EX1164: *Concert Webpage, Understanding Clinical Trial Terminology: What Is A Long-Term Extension Or Open-Label Extension Study?* (Aug. 19, 2020).
PGR2021-00006 EX1165: Richard O. Day & Kenneth M. Williams, *Open-Label Extension Studies: Do They Provide Meaningful Information on the Safety of New Drugs?*, Drug Safety 30(2):93-105 (2007).
PGR2021-00006 EX1166: Karla Hemming et al., *Open label extension studies and patient selection biases*, Journal of Evaluation in Clinical Practice 14:141-144 (2008).
PGR2021-00006 EX1167: G. J. Taylor & P. Wainwright, *Open label extension studies: research or marketing?*, BMJ 331:572-574 (2005).

(56) References Cited

OTHER PUBLICATIONS

PGR2021-00006 EX1168: Concert 2021 slides, *Long-Term Safety & Efficacy of CTP-543, an Oral JAK Inhibitor, for the Potential Treatment of Alopecia Areata.*
PGR2021-00006 EX1169: American Academy of Dermatology Annual Meeting 2020 slides, *New CTP-543 (Oral JAK1/2 Inhibitor) Phase 2 Analyses: SALT 20 was statistically significant from placebo for the 8 and 12 mg BID cohorts in alopecia areata trial.*
PGR2021-00006 EX1170: Transcript of Deposition of Justin Ko, M.D., M.B.A. taken Oct. 29, 2021, in PGR2021-00006.
PGR2021-00006 EX1171: Transcript of Deposition of Paul Ortiz de Montellano, Ph.D. taken Oct. 22, 2021, in PGR2021-00006.
PGR2021-00006 EX1172: Transcript of Deposition of Vinita Uttamsingh, Ph.D. taken Oct. 27, 2021, in PGR2021-00006.
PGR2021-00006 EX1173: International Publication No. WO 2013/188783 (published Dec. 19, 2013).
PGR2021-00006 EX1174: Concert Pharmaceuticals Inc. Q4 2016 Earnings Call (Mar. 6, 2017 Earnings Call Transcript).
PGR2021-00006 EX1175: Concert Pharmaceuticals' (CNCE) CEO Roger Tung on Q1 2016 Results- Earnings Call Transcript, May 5, 2016, https://seekingalpha.com/article/3972790-concert-pharmaceuticals-cnce- ceo-roger-tung-on-q1-2016-results-earnings-call-transcript.
PGR2021-00006 EX1176: Final Written Decision, IPR2017-01256, Paper 119 (PTAB Apr. 8, 2019).
PGR2021-00006 EX1177: Declaration of Raymond O. Cruitt (Nov. 12, 2021).
PGR2021-00006 EX1178: Concert Press Release, Concert Pharmaceuticals Reports Year Ended 2016 Financial Results (Mar. 6, 2017).
PGR2021-00006 EX1179: Concert Fourth Quarter 2016 Earnings Call Transcript (Mar. 6, 2017).
PGR2021-00006 EX1180: Concert First Quarter 2016 Earnings Call Transcript (May 5, 2016).
PGR2021-00006 EX1192: Jan. 6, 2022 Conference Call Transcript.
PGR2021-00006 EX2030: K. P. Huang et al., Autoimmune, Atopic, and Mental Health Comorbid Conditions Associated with Alopecia Areata in the United States, JAMA Dermatol. 149(7):789-794 (2013) ("Huang 2013").
PGR2021-00006 EX2031: A. Alkhalifah et al., Alopecia Areata Update, J. Am. Acad. Dermatol. 192-202 (Feb. 2010) ("Alkhalifah 2010").
PGR2021-00006 EX2035: Declaration of Jerry Shapiro, M.D., IPR2017-01256 (dated Sept. 9, 2018).
PGR2021-00006 EX2036: Declaration of Jerry Shapiro, M.D., IPR2017-01256 (dated Oct. 3, 2018).
PGR2021-00006 EX2037: U. Blume-Peytavi and A. Vogt, Translational Positioning of Janus Kinase (JAK) Inhibitors in Alopecia Areata, Ebio Medicine 2:282-283 (2015) ("Blume-Peytavi").
PGR2021-00006 EX2039: L. Hsu and A. Armstrong, *JAK Inhibitors: Treatment Efficacy and Safety Profile in Patients with Psoriasis*, Journal of Immunology Research (2014) ("Hsu").
PGR2021-00006 EX2040: H. Guo et al., *The Role of Lymphocytes in the Development and Treatment of Alopecia Areata*, Expert Rev. Clin. Immunol. 11(12)1335-1351 (2015) ("Guo").
PGR2021-00006 EX2041: K. Hordinsky, *Current Treatments for Alopecia Areata*, The Journal of Investigative Dermatology Symposium, 17:44-46 (2015) ("Hordinsky 2015").
PGR2021-00006 EX2048: C. Wiegand et al., Dermal Xenobiotic Metabolism: A Comparison between Native Human Skin, Four in vitro Skin Test Systems and a Liver System, Skin Parmacol. Physiol., 27:263-275 (2014) ("Wiegand 2014").
PGR2021-00006 EX2051: A. Gilhar et al., Alopecia areata: Animal models illuminate autoimmune pathogenesis and novel immunotherapeutic strategies, Autoimmune Rev. 15(7):726-735 (Jul. 2016) ("Gilhar 2016").
PGR2021-00006 EX2052: U.S. Pat. No. 10,561,659—Certified Patent Assignment ("Certified Wagner Assignment") (recorded on Nov. 27, 2019).
PGR2021-00006 EX2053: U.S. Pat. No. 9,249, 149—Certified Patent Assignment ("Certified Silverman Assignment") (recorded Jun. 14, 2015).
PGR2021-00006 EX2054: Deposition Transcript of Jerry Shapiro, M.D., dated Jul. 21, 2021.
PGR2021-00006 EX2055: Deposition Transcript of Dr. Steven Patterson, dated Jul. 30, 2021.
PGR2021-00006 EX2056: M. Hordinsky and A. Donati, Alopecia Areata: An Evidence-Based Treatment Update, Am. J. Clin. Dermatol., 15:231-246 (2014) ("Hordinsky 2014").
PGR2021-00006 EX2058: F. Anzegruber et al., Transient Efficacy of Tofacitinib in Alopecia Areata Universalis, Case Rep. Dermatol., 8:102-106 (2016) ("Anzegruber 2016").
PGR2021-00006 EX2059: Declaration of Justin Ko, M.D., M.B.A. (dated Aug. 12, 2021).
PGR2021-00006 EX2060: Declaration of Kimberly A. Mack (dated Aug. 10, 2021).
PGR2021-00006 EX2062: E. Olsen et al., Ruxolitinib cream for the treatment of patients with alopecia areata: A 2-part, double-blind, randomized, vehicle-controlled phase 2 study 2020, J. Am. Acad. Dermatol., 82(2):412-419 (Feb. 2020) ("Olsen 2020").
PGR2021-00006 EX2063: J. A. Palanivel et al., An Insight into JAK-STAT signalling in Dermatology, Clinical and Experimental Dermatology, 39:513-518 (2014).
PGR2021-00006 EX2064: Y. Furumoto and M. Gadina, The Arrival of JAK inhibitors: Advancing the Treatment of Immune and Hematologic Disorders, BioDrugs, 27(5):431-438 (2013).
PGR2021-00006 EX2065: R. M. Trüeb et al., A Comment on JAK Inhibitors for Treatment of Alopecia Areata, Int. J. Trichology, 10(5): 193-197 (Sep-Oct. 2018), available at: A Comment on JAK Inhibitors for Treatment of Alopecia Areata—PubMed (nih.gov).
PGR2021-00006 EX2066: B. May, Incyte's Ruxolitinib Cream Shows Promise for Vitiligo in Phase III Trials, BioSpace (May 17, 2021), available at: https://www.biospace.com/article/incyte-s-ruxolitinib-cream-shows- promise-for-vitiligo-in-phase-iii-trials/.
PGR2021-00006 EX2067: E. Sagonowsky, Incyte hits 2nd FDA delay in span of days, this time for atopic dermatitis hopeful ruxolitinib cream, FiercePharma (Jun. 11, 2021), available at: https://www.fiercepharma.com/pharma/incyte-hit-2nd-fda-delay- span-days-time-for-atopic-dermatitis-med-ruxolitinib-cream.
PGR2021-00006 EX2068: Declaration of Paul Ortiz de Montellano (dated Aug. 11, 2021).
PGR2021-00006 EX2069: Declaration of Vinita Uttaminsingh In Support of Concert's Patent Owner Response (dated Aug. 10, 2021).
PGR2021-00006 EX2070: Declaration of Julie F. Liu (dated Aug. 6, 2021).
PGR2021-00006 EX2071: Declaration of Scott L. Harbeson (dated Aug. 10, 2021).
PGR2021-00006 EX2072: Declaration of Adam Morgan (dated Aug. 10, 2021).
PGR2021-00006 EX2073: Excerpts of slides from Concert Quarterly Update Meeting (Dec. 3, 2013).
PGR2021-00006 EX2074: Bertram G. Katzung et al., Basic & Clinical Pharmacology, 1, 43-44 (11th ed., McGraw Hill 2009) ("Katzung 2009").
PGR2021-00006 EX2075: Declaration of F. Peter Guengerich, Ph.D. In Support of Petition for Inter Partes Review of Claims 1-15 of U.S. Pat. No. 9,249,149, IPR2017-01256 (dated Apr. 7, 2017).
PGR2021-00006 EX2076: N. Islam et al., The Autoimmune Basis of Alopecia Areata: A Comprehensive Review, Autoimmunity Reviews 14:81-89 (2015) ("Islam 2015").
PGR2021-00006 EX2077: B. G. Craiglow and B. A. King, Killing Two Birds with One Stone: Oral Tofacitinib Reverses Alopecia Universalis in a Patient with Plaque Psoriasis, Journal of Investigative Dermatology, 134:2988-2990 (2014).
PGR2021-00006 EX2078: B. G. Craiglow et al., Topical Ruxolitinib for the Treatment of Alopecia Universalis, JAMA Dermatology, 152(4):490-491 (Apr. 2016) ("Craiglow 2016").
PGR2021-00006 EX2079: U. Zanger and M. Schwab, Cytochrome P450 enzymes in drug metabolism: Regulation of gene expression, enzyme activities, and impact of genetic variation, Pharmacology & Therapeutics, 138:103-141 (2013) ("Zanger 2013").

(56) References Cited

OTHER PUBLICATIONS

PGR2021-00006 EX2080: T. Nissen and R. Wynn, The Clinical Case Report: A Review of its Merits and Limitations, BMC Research Notes, 7:264 (2014).
PGR2021-00006 EX2081: Lilly and Incyte's Baricitinib Improved Hair Regrowth for Alopecia Areata Patients in Second Phase 3 Study (Apr. 20, 2021), available at: Lilly and Incyte's Baricitinib Improved Hair Regrowth for Alopecia Areata Patients in Second Phase 3 Study | Eli Lilly and Company.
PGR2021-00006 EX2082: Baricitinib is First JAK-Inhibitor to Demonstrate Hair Regrowth in Phase 3 Alopecia Areata (AA) Trial (Mar. 3, 2021), available at: Baricitinib is First JAK-Inhibitor to Demonstrate Hair Regrowth in Phase 3 Alopecia Areata (AA) Trial | Eli Lilly and Company.
PGR2021-00006 EX2083: CP543.5001 Patient Tracker (submitted Aug. 12, 2021).
PGR2021-00006 EX2084: Concert Pharmaceuticals, Inc., CTP-543, Protocol No. CP543.1007 (Draft) (submitted Aug. 12, 2021).
PGR2021-00006 EX2085: N. Atanaskova, Hot Off the Press! Another Treatment Shows Promise in Alopecia Areata (Dec. 3, 2015), available at: https://www.naaf.org/news-room/hot-off-the-press-another- treatment-shows-promise-in-alopecia-areata.
PGR2021-00006 EX2086: Calendar Invitation for Dec. 3, 2013 Quarterly Meeting Update.
PGR2021-00006 EX2094: Ansel's Pharmaceutical Dosage Forms and Drug Delivery Systems, Chapter 9 (8th ed., Lippincott Williams & Wilkins 2005.
PGR2021-00006 EX2095: Clinical Drug Interaction Studies—Cytochrome P450 Enzyme-and Transporter-Mediated Drug Interactions Guidance for Industry FDA Guidance, U.S. Department of Health and Human Services, FDA CDER (Jan. 2020), available at: https://www.fda.gov/media/134581/download ("FDA Guidance").
PGR2021-00006 EX2096: Drug Development and Drug Interactions, Table of Substrates, Inhibitors and Inducers, FDA, available at: https://www.fda.gov/drugs/drug-interactions-labeling/drug-development-and-drug-interactions-table-substrates-inhibitors-and-inducers#table3-2 (Aug. 3, 2021).
PGR2021-00006 EX2097: Sporanox® (itraconazole) Capsules Label (Physicians' Desk Reference, 59th ed. 2005).
PGR2021-00006 EX2098: Nizoral® (ketoconazole) Label, Rev. Jul. 2013.
PGR2021-00006 EX2099: Tissue expression of CYP2C9—Staining in Skin, The Human Protein Atlas, available at: https://web.archive.org/web/20150610174247/https://www.proteinatlas.org/ENSG00000138109-CYP2C9/tissue/skin ("Protein Atlas—2C9") (Aug. 12, 2021); ;.
PGR2021-00006 EX2100: Tissue expression of CYP3A4—Staining in Skin, The Human Protein Atlas, available at: https://web.archive.org/web/20160330230102/https://www.proteinatlas.org/ENSG00000160868-CYP3A4/tissue/skin ("Protein Atlas—3A4") (Aug. 3, 2021).
PGR2021-00006 EX2101: K. Bui et al., Successful Treatment of Alopecia Universalis With Alefacept: A Case Report and Review of the Literature, Cutis, 81(5):431-434 (2008) ("Bui 2008").
PGR2021-00006 EX2102: B. E. Strober et al., *Alefacept for Severe Alopecia Areata: A Randomized, Double-blind, Placebo-Controlled Study*, Arch. Dermatol. 145(11):1262-1266 (2009) ("Strober 2009").
PGR2021-00006 EX2103: K. Gorcey et al., *Alopecia Universalis Successfully Treated With Adalimumab*, JAMA Dermatol. 150(12): 1341-1344 (Dec. 2014) ("Gorcey 2014").
PGR2021-00006 EX2104: B. E. Strober et al., *Etanercept Does Not Effectively Treat Moderate to Severe Alopecia Areata: An Open-Label Study*, J. Am. Acad. Dermatol. 52(6): 1082-1084 (Jun. 2005) ("Strober 2005").
PGR2021-00006 EX2105: N. A. Mesinkovska amd W. F. Bergfeld, *Universal Protocol for Alopecia Areata Clinical Studies*, Journal of Investigative Dermatology Symposium Proceedings, 16:S48 (2013) ("Mesinkovska 2013").
PGR2021-00006 EX2106: I. A. Seo et al., *Janus Kinase 2 Inhibitor AG490 Inhibits the STAT3 Signaling Pathway by Suppressing Protein Translation of gp130 2009*, Korean J. Physiol. Pharmacol. 13:131-138 (Apr. 2009) ("Seo 2009").
PGR2021-00006 EX2107: Clinical Trial Listing, A Study of Baricitinib (LY3009104) in Participants With Severe or Very Severe Alopecia Areata (BRAVE-AA1), available at: https://clinicaltrials.gov/ct2/show/NCT03570749 (Aug. 9, 2021).
PGR2021-00006 EX2108: Clinical Trial Listing, A Study of Baricitinib (LY3009104) in Adults With Severe or Very Severe Alopecia Areata (BRAVE-AA2), available at: https://clinicaltrials.gov/ct2/show/NCT03899259 (Aug. 9, 2021).
PGR2021-00006 EX2109: Clinical Trial Listing, A Phase 2 Durability of Response Study of CTP-543 in Adult Patients With Moderate to Severe Alopecia Areata, available at: https://clinicaltrials.gov/ct2/show/NCT04784533 (Aug. 12, 2021).
PGR2021-00006 EX2110: Curriculum Vitae of Paul R. Ortiz de Montellano (Aug. 1, 2021).
PGR2021-00006 EX2111: Cyprotex Cytochrome P450 Ki Product Sheet (submitted Aug. 12, 2021).
PGR2021-00006 EX2112: M. A. Gibbs et al., *Inhibition of Cytochrome P-450 3A (CYP3A) In Human Intestinal and Liver Microsomes: Comparison of Ki Values and Impact of CYP3A5 Expression*, Drug Metabolism and Disposition 27(2):180-187 (1999) ("Gibbs 1999").
PGR2021-00006 EX2113: S. A. Wrighton and B. J. Ring, *Inhibition of Human CYP3A Catalyzed 1'-Hydroxy Midazolam Formation by Ketoconazole, Nifedipine, Erythromycin, Cimetidine, and Nizatidine*, Pharmaceutical Research 11(6):921-924 (1994) ("Wrighton 1994").
PGR2021-00006 EX2114: H. S. Brown, *Evaluation of Cryopreserved Human Hepatocytes as an Alternative in Vitro System to Microsomes for the Prediction of Metabolic Clearance*, Drug Metabolism and Disposition 35(2):293301 (2007) ("Brown 2007").
PGR2021-00006 EX2115: M. Isoherranen et al., Role of Itraconazole Metabolites in CYP3A4 Inhibition, Drug Metabolism and Disposition 32(10):1121-1131 (2004) ("Isoherranen 2004").
PGR2021-00006 EX2116: Y. Chen et al., *Recommendations for the Design of Clinical Drug-Drug Interaction Studies With Itraconazole Using a Mechanistic Physiologically-Based Pharmacokinetic Model*, CPT Pharmacometrics Syst. Pharmacol. 8:685-695 (2019) ("Chen 2019").
PGR2021-00006 EX2117: R. J. Tallarida, Quantitative Methods for Assessing Drug Synergism, Genes and Cancer 2(11):1003-1008 (2011) ("Tallarida 2011").
PGR2021-00006 EX2118: Declaration of James V. Cassella In Support of Concert's Patent Owner Response (dated Aug. 6, 2021).
PGR2021-00006 EX2119: R. Verstovsek et al., Sustained-release ruxolitinib: Findings from a phase 1 study in healthy subjects and a phase 2 study in patients with myelofibrosis, Hematological Oncology 36:701-708 (2018) ("Verstovsek 2018").
PGR2021-00006 EX2120: R. Fleischmann et al., Placebo Controlled Trial of Tofacitinib Monotherapy in Rheumatoid Arthritis, N. Engl. J. Med. 367(6):495507 (Aug. 9, 2012) ("Fleischmann 2012").
PGR2021-00006 EX2121: Curriculum Vitae of Justin M. Ko, M.D., M.B.A. (submitted Aug. 12, 2021).
PGR2021-00006 EX2122: Clinical Trial Listing, A Study of Secukinumab for the Treatment of Alopecia Areata, available at: https://clinicaltrials.gov/ct2/show/NCT02599129?cond=Alopecia+Areata&strd_s=01%2F01%2F2014&strd_e=05%2F16%2F2016&draw=2&rank=1 (Aug. 11, 2021).
PGR2021-00006 EX2123: Cosentyx® (secukinumab) Highlights of Prescribing Information, Rev. Jan. 2016.
PGR2021-00006 EX2124: Clinical Trial Listing, Pilot Study of the Safety and Efficacy of Apremilast in Subjects With Moderate to Severe Alopecia Areata, available at: https://clinicaltrials.gov/ct2/show/NCT02684123?cond=Alopecia+Areata&strd_s=01%2F01%2F2014&strd_e=05%2F16%2F2016&draw=2&rank=3 (Aug. 11, 2021).
PGR2021-00006 EX2125: Clinical Trial Listing, A Pilot Study of Tralokinumab in Subjects With Moderate to Severe Alopecia Areata, available at: https://clinicaltrials.gov/ct2/show/NCT02684097?cond=Alopecia+ ; Areata&strd_s=01%2F01%2F2014&strd_e=05%2F16%2F2016&draw=2&rank=6 (Aug. 11, 2021) ;.
PGR2021-00006 EX2126: Clinical Trial Listing, TREg Activation in the Treatment of the PELADE (Alopecia Areata) (TreatPelade), available at: https://clinicaltrials.gov/ct2/show/NCT02557074?cond=

(56) References Cited

OTHER PUBLICATIONS

Alopecia+; Areata&strd_s=01%2F01%2F2014&strd_e=05%2F16%2F2016&draw=2&rank=10 (Aug. 11, 2021);.
PGR2021-00006 EX2127: Clinical Trial Listing, An Open-Label Single-Arm Clinical Trial to Evaluate The Efficacy of Abatacept in Moderate to Severe Patch Type Alopecia Areata, available at: https://clinicaltrials.gov/ct2/show/NCT02018042?term=abatacept&cond=Alopecia+Areata&dra w=2&rank=1 (Aug. 11, 2021).
PGR2021-00006 EX2128: Orencia (abatacept) Highlights of Prescribing Information, Rev. Dec. 2013.
PGR2021-00006 EX2129: H. Almohanna et al., Platelet-Rich Plasma in the Treatment of Alopecia Areata: A Review, Journal of Investigative Dermatology Symposium Proceedings 20:S45-S49 (2020) ("Almohanna 2020").
PGR2021-00006 EX2130: Incyte Corporation Form 10-K, dated Feb. 12, 2016.
PGR2021-00006 EX2131: Humira (adalimumab) Highlights of Prescribing Information, Rev. Nov. 2015.
PGR2021-00006 EX2132: FDA Statement on the Voluntary Withdrawal of Raptiva From the U.S. Market (Apr. 8, 2009), available at: https://www.fda.gov/drugs/postmarket-drug-safety-information-patients-and providers/fda-statement-voluntary-withdrawal-raptiva- us-market ("FDA Announcement").
PGR2021-00006 Paper 22 Patent Owner's Objections to Petitioner's Evidence Submitted with Petition for Post-Grant Review (May 25, 2021).
PGR2021-00006 Paper 23 Patent Owner's Motion for Rehearing Pursuant to 37 C.F.R Section 42.71 (May 25, 2021).
PGR2021-00006 Paper 24 Petitioner's Objections to Evidence (May 26, 2021).
PGR2021-00006 Paper 25 Denying Patent Owner's Request for Rehearing (Jun. 9, 2021).
PGR2021-00006 Paper 39 Petitioner's Objections to Evidence (Aug. 19, 2021).
PGR2021-00006 Paper 4 Notice to Accord Filing Date (Nov. 18, 2020).
PGR2021-00006 Paper 49 Patent Owner's Objections to Petitioner's Evidence Submitted with Petitioner's Reply to Patent Owner's Response (Nov. 19, 2021).
PGR2021-00006 Paper 51 Patent Owner's Sur-Reply to Petitioner's Reply to Patent Owner Response Petition (Dec. 13, 2021).
PGR2021-00006 Paper 55 Patent Owner's Motion to Exclude Evidence (Jan. 12, 2022).
PGR2021-00006 Paper 56 Petitioner's Motion to Exclude (Jan. 12, 2022).
PGR2021-00006 Paper 59 Patent Owner's Opposition to Petitioner's Motion to Exclude (Jan. 19, 2022).
PGR2021-00006 Paper 60 Petitioner's Opposition to Patent Owner's Motion to Exclude (Jan. 19, 2022).
PGR2021-00006 Paper 61 Patent Owner's Reply to Petitioner's Opposition to Patent Owner's Motion to Exclude (Jan. 26, 2022).
PGR2021-00006 Paper 62 Petitioner's Reply to Patent Owner's Opposition to Petitioner's Motion to Exclude (Jan. 26, 2022).
PGR2021-00006 Paper 65 Patent Owner's Demonstratives (Feb. 8, 2022).
PGR2021-00006 Paper 66 Petitioner's Demonstratives (Feb. 8, 2022).
PGR2021-00006 Paper 47 Oral Hearing Transcript (Apr. 27, 2022).
PGR2021-00006 Paper 68 Final Written Decision (May 11, 2022).
PGR2021-00006 Paper 69 Petitioner's Request for Rehearing (Jun. 10, 2022).
PGR2021-00006 Paper 70 Decision Denying Petitioner's Request for Rehearing of Final Written Decision (Oct. 11, 2022).
Appeal of Final Written Decision for PGR 2021-00006; Appellee's Principal Brief (Corrected); Filed Sep. 10, 2023.
Appeal of Final Written Decision for PGR 2021-00006; Corrected Non-Confidential Opening Brief of Incyte Corporation; Filed Aug. 14, 2023.
Appeal of Final Written Decision for PGR 2021-00006; Non-Confidential Reply Brief of Incyte Corporation; Filed Nov. 13, 2023.
U.S. Appl. No. 16/098,338, Granted as U.S. Pat. No. 10,561,659.

\* cited by examiner

Mean (CV%) Single Ascending Dose PK Parameters

| CTP-543 Dose | $C_{max}$ (nM) | $T_{max}^a$ (hr) | $T_{1/2}$ (hr) | $AUC_{0-inf}$ (nM*hr) | CL/F (L/hr) |
|---|---|---|---|---|---|
| 8 mg | 376 (28%) | 1.25 (0.5-1.5) | 3.1 (29%) | 1875 (32%) | 14.9 (35%) |
| 16 mg | 687 (24%) | 1.75 (0.5-3.0) | 3.3 (26%) | 3959 (30%) | 14.5 (47%) |
| 32 mg | 1702 (29%) | 1.25 (0.5-2.0) | 3.5 (16%) | 7831 (26%) | 13.9 (30%) |
| 48 mg | 2714 (26%) | 1.50 (0.5-2.0) | 3.6 (21%) | 13237 (35%) | 12.7 (34%) |

*Data presented are preliminary results; $^a$ Median values (range)*

FIG. 1C

Mean (CV%) Multiple Ascending Dose Steady-State PK Parameters

| CTP-543 Dose | $C_{max}$ (nM) | $T_{max}{}^a$ (hr) | $T_{1/2}$ (hr) | $AUC_{0-24}$ (nM*hr) | $CL_{ss}/F$ (L/hr) |
|---|---|---|---|---|---|
| 8 mg QD | 480 (34%) | 1.0 (0.25-1.5) | 3.5 (21%) | 2131 (28%) | 12.7 (25%) |
| 24 mg QD | 986 (23%) | 1.0 (0.5-2.0) | 3.5 (25%) | 4868 (25%) | 16.5 (22%) |
| 32 mg QD | 1564 (18%) | 0.75 (0.5-2.0) | 3.5 (37%) | 6684 (28%) | 16.5 (33%) |

| CTP-543 Dose | $C_{max}$ (nM) | $T_{max}{}^a$ (hr) | $T_{1/2}$ (hr) | $AUC_{0-12}$ (nM*hr) | $CL_{ss}/F$ (L/hr) |
|---|---|---|---|---|---|
| 8 mg BID | 564 (24%) | 1.5 (0.25-2.0) | 3.9 (34%) | 2615 (36%) | 10.7 (34%) |
| 16 mg BID | 917 (36%) | 0.75 (0.5-2.0) | 3.5 (19%) | 3577 (26%) | 15.0 (24%) |

*Data presented are preliminary results;* $^a$ *Median values (range)*

FIG. 2C

TREATMENT OF HAIR LOSS DISORDERS WITH DEUTERATED JAK INHIBITORS

RELATED APPLICATIONS

This application is a continuation of U.S. application Ser. No. 16/098,338, filed on Nov. 1, 2018, which is the U.S. National Stage of International Application No. PCT/US2017/31142, filed on May 4, 2017, published in English, which claims the benefit of U.S. Provisional Application No. 62/331,827, filed on May 4, 2016, 62/338,869, filed on May 19, 2016, 62/418,774, filed on Nov. 7, 2016, 62/419,237, filed on Nov. 8, 2016, 62/434,404, filed on Dec. 14, 2016, 62/466,358, filed on Mar. 2, 2017 and 62/492,758, filed on May 1, 2017. The entire teachings of the above applications are incorporated herein by reference.

BACKGROUND OF THE INVENTION

Many current medicines suffer from poor absorption, distribution, metabolism and/or excretion (ADME) properties that prevent their wider use or limit their use in certain indications. Poor ADME properties are also a major reason for the failure of drug candidates in clinical trials. While formulation technologies and prodrug strategies can be employed in some cases to improve certain ADME properties, these approaches often fail to address the underlying ADME problems that exist for many drugs and drug candidates. One such problem is rapid metabolism that causes a number of drugs, which otherwise would be highly effective in treating a disease, to be cleared too rapidly from the body. A possible solution to rapid drug clearance is frequent or high dosing to attain a sufficiently high plasma level of drug. This, however, introduces a number of potential treatment problems such as poor patient compliance with the dosing regimen, side effects that become more acute with higher doses, and increased cost of treatment. A rapidly metabolized drug may also expose patients to undesirable toxic or reactive metabolites.

Another ADME limitation that affects many medicines is the formation of toxic or biologically reactive metabolites. As a result, some patients receiving the drug may experience toxicities, or the safe dosing of such drugs may be limited such that patients receive a suboptimal amount of the active agent. In certain cases, modifying dosing intervals or formulation approaches can help to reduce clinical adverse effects, but often the formation of such undesirable metabolites is intrinsic to the metabolism of the compound.

In some select cases, a metabolic inhibitor will be co-administered with a drug that is cleared too rapidly. Such is the case with the protease inhibitor class of drugs that are used to treat HIV infection. The FDA recommends that these drugs be co-dosed with ritonavir, an inhibitor of cytochrome P450 enzyme 3A4 (CYP3A4), the enzyme typically responsible for their metabolism (see Kempf, D. J. et al., Antimicrobial agents and chemotherapy, 1997, 41(3): 654-60). Ritonavir, however, causes adverse effects and adds to the pill burden for HIV patients who must already take a combination of different drugs. Similarly, the CYP2D6 inhibitor quinidine has been added to dextromethorphan for the purpose of reducing rapid CYP2D6 metabolism of dextromethorphan in a treatment of pseudobulbar affect. Quinidine, however, has unwanted side effects that greatly limit its use in potential combination therapy (see Wang, L et al., Clinical Pharmacology and Therapeutics, 1994, 56(6 Pt 1): 659-67; and FDA label for quinidine at www.accessdata.fda.gov).

In general, combining drugs with cytochrome P450 (CYP) inhibitors is not a satisfactory strategy for decreasing drug clearance. The inhibition of a CYP enzyme's activity can affect the metabolism and clearance of other drugs metabolized by that same enzyme. CYP inhibition can cause other drugs to accumulate in the body to toxic levels.

A potentially attractive strategy for improving a drug's metabolic properties is deuterium modification. In this approach, one attempts to slow the CYP-mediated metabolism of a drug or to reduce the formation of undesirable metabolites by replacing one or more hydrogen atoms with deuterium atoms. Deuterium is a safe, stable, non-radioactive isotope of hydrogen. Compared to hydrogen, deuterium forms stronger bonds with carbon. In select cases, the increased bond strength imparted by deuterium can positively impact the ADME properties of a drug, creating the potential for improved drug efficacy, safety, and/or tolerability. At the same time, because the size and shape of deuterium are essentially identical to those of hydrogen, replacement of hydrogen by deuterium would not be expected to affect the biochemical potency and selectivity of the drug as compared to the original chemical entity that contains only hydrogen.

Over the past 35 years, the effects of deuterium substitution on the rate of metabolism have been reported for a very small percentage of approved drugs (see, e.g., Blake, M I et al, J Pharm Sci, 1975, 64:367-91; Foster, AB, Adv Drug Res, 1985, 14:1-40 ("Foster"); Kushner, D J et al, Can J Physiol Pharmacol, 1999, 79-88; Fisher, M B et al, Curr Opin Drug Discov Devel, 2006, 9:101-09 ("Fisher")). The results have been variable and unpredictable. For some compounds deuteration caused decreased metabolic clearance in vivo. For others, there was no change in metabolism. Still others demonstrated increased metabolic clearance. The variability in deuterium effects has also led experts to question or dismiss deuterium modification as a viable drug design strategy for inhibiting adverse metabolism (see Foster at p. 35 and Fisher at p. 101).

The effects of deuterium modification on a drug's metabolic properties are not predictable even when deuterium atoms are incorporated at known sites of metabolism. Only by actually preparing and testing a deuterated drug can one determine if and how the rate of metabolism will differ from that of its non-deuterated counterpart. See, for example, Fukuto et al. (J. Med. Chem., 1991, 34, 2871-76). Many drugs have multiple sites where metabolism is possible. The site(s) where deuterium substitution is required and the extent of deuteration necessary to see an effect on metabolism, if any, will be different for each drug.

Ruxolitinib phosphate, is a heteroaryl-substituted pyrrolo[2,3-d]pyrimidines also known as 3(R)-cyclopentyl-3-[4-(7H-pyrrolo[2,3-d]pyrimidin-4-yl)-1H-pyrazol-1-yl]propanenitrile phosphate and as (R)-3-(4-(7H-pyrrolo[2,3-d]pyrimidin-4-yl)-1H-pyrazol-1-yl)-3-cyclopentylpropanenitrile phosphate, inhibits Janus Associated Kinases (JAKs) JAK1 and JAK2. These kinases mediate the signaling of a number of cytokines and growth factors important for hematopoiesis and immune function. JAK signaling involves recruitment of STATs (signal transducers and activators of transcription) to cytokine receptors, activation and subsequent localization of STATs to the nucleus leading to modulation of gene expression.

Ruxolitinib phosphate is currently approved for the treatment of patients with intermediate or high-risk myelofibrosis, including primary myelofibrosis, post-polycythemia vera myelofibrosis and post-essential thrombocythemia myelofibrosis. Ruxolitinib phosphate is also currently in clinical trials for the treatment of additional conditions.

Despite the beneficial activities of ruxolitinib, there is a continuing need for new compounds to treat the aforementioned diseases and conditions.

SUMMARY OF THE INVENTION

It has now been found that deuterated analogs of ruxolitinib (including Compound (I), also referred to as (R)-3-(4-(7H-pyrrolo[2,3-d]pyrimidin-4-yl)-1H-pyrazol-1-yl)-3-(cyclopentyl-2,2,3,3,4,4,5,5-d$_8$)propanenitrile, or D8-ruxolitinib), are useful for the treatment of hair-loss disorders, including alopecia areata. Compound (I) is represented by the following structural formula:

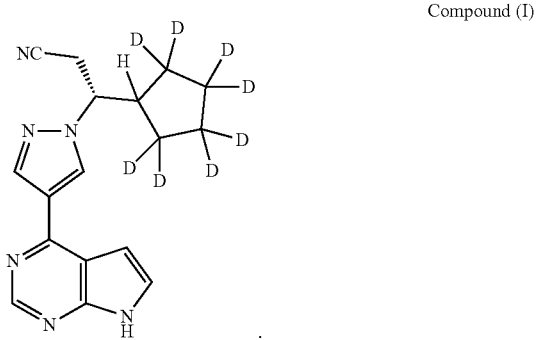 [SMILES: [2H]C1([2H])C([C@@H](CC#N)n2cc(-c3ncnc4[nH]ccc34)cn2)C([2H])([2H])C([2H])([2H])C1([2H])[2H]]

Compound (I)

In certain embodiments, Compound (I) is administered as a pharmaceutically acceptable salt, such as the phosphate salt. Compound (I) can be administered in doses in the range of about 4 mg to about 50 mg per day (or the equivalent weight based on a salt, such as Compound (I) phosphate salt), administered as a single daily dose or in divided doses (e.g., twice per day). Based on these discoveries, novel therapies using Compound (I) or a pharmaceutically acceptable salt thereof, for treating a hair loss disorder in a mammalian subject are disclosed herein.

One aspect of the invention is a method for treating hair loss disorders that can be treated by compounds that modulate the activity of Janus Associated Kinase 1 (JAK1) and/or Janus Associated Kinase 2 (JAK2). The method comprises administering to a subject (e.g., a mammalian subject) an effective amount of Compound (I), or a pharmaceutically acceptable salt thereof (i.e., an equivalent amount of a pharmaceutically acceptable salt, such as the phosphate salt)), once or twice per day, wherein the amount of Compound (I), or a pharmaceutically acceptable salt thereof, is in the range of about 4 mg/day to about 50 mg/day, for example, about 5 mg/day, about 10 mg/day, about 20 mg/day, about 30 mg/day, about 40 mg/day, or about 50 mg/day. In certain embodiments, the amount of Compound (I), or a pharmaceutically acceptable salt thereof, is about 4 mg/day, 8 mg/day, 16 mg/day, 32 mg/day or 48 mg/day. In certain embodiments, the amount of Compound (I), or a pharmaceutically acceptable salt thereof, is 8 mg/day, 16 mg/day, 24 mg/day, or 32 mg/day. In certain embodiments, the amount of Compound (I), or a pharmaceutically acceptable salt thereof, is 8 mg/day, 16 mg/day, 24 mg/day, or 32 mg/day. In certain embodiments, the amount of Compound (I), or a pharmaceutically acceptable salt thereof is 4 mg, 8 mg, 12 mg or 16 mg twice per day. In certain embodiments, the hair loss disorder is alopecia areata. In certain embodiments, the subject is a human. Preferably, Compound (I), or a pharmaceutically acceptable salt thereof (such as the phosphate salt), is administered orally at any of the foregoing dosages. Preferably, the Compound (I), or a pharmaceutically acceptable salt thereof, is administered orally at any of the foregoing dosages in a pharmaceutical formulation which is a tablet.

In an alternative aspect, the invention provides a method for treating hair loss disorders, the method comprising topically administering to a subject (e.g., a mammalian subject) an effective amount of Compound (I), or a pharmaceutically acceptable salt thereof (i.e., an equivalent amount of a pharmaceutically acceptable salt, such as the phosphate salt). In certain embodiments, the compound is administered in a pharmaceutical composition which is formulated for topical administration, such as a cream, ointment, lotion, foam or the like.

In another aspect, the invention provides a method for inducing hair growth in a subject. The method comprises administering to a mammalian subject an effective amount of Compound (I), or a pharmaceutically acceptable salt thereof (i.e., an equivalent amount of a pharmaceutically acceptable salt, such as the phosphate salt), once or twice per day, wherein the amount of Compound (I), or a pharmaceutically acceptable salt thereof, is in the range of about 4 mg/day to about 50 mg/day, for example, about 5 mg/day, about 10 mg/day, about 20 mg/day, about 30 mg/day, about 40 mg/day, or about 50 mg/day. In certain embodiments, the amount of Compound (I), or a pharmaceutically acceptable salt thereof, is about 4 mg/day, 8 mg/day, 16 mg/day, 32 mg/day or 48 mg/day. In certain embodiments, the amount of Compound (I), or a pharmaceutically acceptable salt thereof, is 8 mg/day, 16 mg/day, 24 mg/day, or 32 mg/day. In certain embodiments, the subject suffers from a hair loss disorder; in further embodiments, the hair loss disorder is alopecia areata. In certain embodiments, the subject is a human. In one embodiment, the subject is a human 6 years of age or older. Preferably, Compound (I), or a pharmaceutically acceptable salt thereof (such as the phosphate salt), is administered orally at any of the foregoing dosages. Preferably, the Compound (I), or a pharmaceutically acceptable salt thereof, is administered orally at any of the foregoing dosages in a pharmaceutical formulation which is a tablet.

Another aspect of the invention is a method for treating autoimmune skin disorders disorders that can be treated by compounds that modulate the activity of Janus Associated Kinase 1 (JAK1) and/or Janus Associated Kinase 2 (JAK2). The method comprises administering to a subject (e.g., a mammalian subject) an effective amount of Compound (I), or a pharmaceutically acceptable salt thereof (i.e., an equivalent amount of a pharmaceutically acceptable salt, such as the phosphate salt), once or twice per day, wherein the amount of Compound (I), or a pharmaceutically acceptable salt thereof, is in the range of about 4 mg/day to about 50 mg/day, for example, about 5 mg/day, about 10 mg/day, about 20 mg/day, about 30 mg/day, about 40 mg/day, or about 50 mg/day. In certain embodiments, the amount of Compound (I), or a pharmaceutically acceptable salt thereof, is about 4 mg/day, 8 mg/day, 16 mg/day, 32 mg/day or 48 mg/day. In certain embodiments, the amount of Compound (I), or a pharmaceutically acceptable salt thereof, is 8 mg/day, 16 mg/day, 24 mg/day, or 32 mg/day. In certain embodiments, the amount of Compound (I), or a pharmaceutically acceptable salt thereof, is 8 mg/day, 16 mg/day, 24 mg/day, or 32 mg/day. In certain embodiments, the amount of Compound (I), or a pharmaceutically acceptable salt thereof is 4 mg, 8 mg, 12 mg or 16 mg twice per day. In certain embodiments, the autoimmune skin disorder is alopecia areata, vitiligo, atopic dermatitis (ezcema), or psoriasis. In certain embodiments, the subject is a human. Preferably, Compound (I), or a pharmaceutically acceptable salt thereof (such as the phosphate salt), is administered orally at any of the foregoing dosages. Preferably, the Compound (I), or a pharmaceutically acceptable salt thereof, is administered orally at any of the foregoing dosages in a pharmaceutical formulation which is a tablet.

Another aspect of the invention is Compound (I), or a pharmaceutically acceptable salt thereof (i.e., an equivalent amount of a pharmaceutically acceptable salt, such as the phosphate salt), for use in treating hair loss disorders that can be treated by compounds that modulate the activity of Janus kinase 1 (JAK1) and/or Janus kinase 2 (JAK2). The compound may be administered at the dosing regimens disclosed herein. In certain embodiments, the hair loss disorder is alopecia areata.

Still another aspect of the invention is the use of Compound (I), or a pharmaceutically acceptable salt thereof (i.e., an equivalent amount of a pharmaceutically acceptable salt, such as the phosphate salt), for the manufacture of a medicament for method for treating hair loss disorders that can be treated by compounds that modulate the activity of Janus Associated Kinase 1 (JAK1) and/or Janus Associated Kinase 2 (JAK2). The compound may be administered at the dosing regimens disclosed herein. In certain embodiments, the hair loss disorder is alopecia areata.

Another aspect of the invention is a pharmaceutical composition comprising Compound (I), in the range of about 4 mg to about 50 mg (for example, about 5 mg, about 10 mg, about 20 mg, about 30 mg, about 40 mg, or about 50 mg), or an equivalent amount of a pharmaceutically acceptable salt thereof (i.e., an equivalent amount of a pharmaceutically acceptable salt, such as the phosphate salt), together with a pharmaceutically acceptable carrier or diluent. In certain embodiments, the amount of Compound (I), or a pharmaceutically acceptable salt thereof, is about 4 mg, 8 mg, 16 mg, 24 mg, 32 mg or 48 mg. In certain embodiments, the amount of Compound (I), or a pharmaceutically acceptable salt thereof, is 4 mg, 8 mg, 12 mg, or 16 mg. In certain embodiments, the pharmaceutical composition is a tablet.

BRIEF DESCRIPTION OF THE DRAWINGS

FIG. 1C is a table showing mean PK parameters for CTP-543 (Compound (I)) in the SAD study.

FIG. 2C is a table showing mean PK parameters for CTP-543 (Compound (I)) in the MAD study.

DETAILED DESCRIPTION OF THE INVENTION

Definitions

Figure 1A:
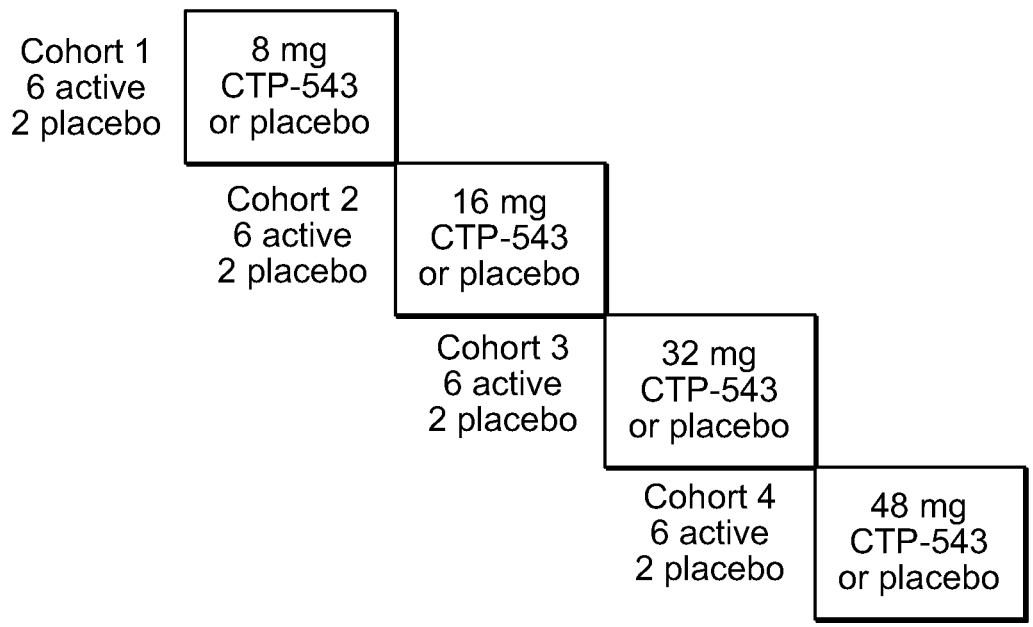
FIG. 1A depicts a study design for a single ascending dose (SAD) trial in healthy volunteers.

The term "treat" means decrease, suppress, attenuate, diminish, arrest, or stabilize the development or progression of a disease (e.g., a disease or disorder delineated herein), lessen the severity of the disease or improve the symptoms associated with the disease. For example, treatment of a hair loss disorder includes regrowth of hair, prevention of further hair loss, or diminishing the rate of hair loss.

"Hair loss disorder" means any condition or disorder that results in loss of hair on one or more areas of the body. Hair loss disorders include, without limitation, androgenetic alopecia, alopecia areata, telogen effluvium, alopecia areata, alopecia totalis, and alopecia universalis.

The term "mammal", as used herein, includes humans, as well as non-human mammals such as cats, dogs, sheep, cattle, pigs, goats, non-human primates (including monkeys and apes) and the like.

It will be recognized that some variation of natural isotopic abundance occurs in a synthesized compound depending upon the origin of chemical materials used in the synthesis. Thus, a preparation of ruxolitinib will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada, E et al., Seikagaku, 1994, 66:15; Gannes, L Z et al., Comp Biochem Physiol Mol Integr Physiol, 1998, 119:725.

In Compound (I), any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3000 times greater than the natural abundance of deuterium, which is 0.015% (i.e., at least 45% incorporation of deuterium).

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "isotopologue" refers to a species in which the chemical structure differs from Compound (I) only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound.

The invention also provides salts of Compound (I). A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt, such as a phosphate salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" and "d" both refer to deuterium. "Stereoisomer" refers to both enantiomers and diastereomers. "Tert" and "t-" each refer to tertiary. "US" refers to the United States of America.

"Substituted with deuterium" refers to the replacement of one or more hydrogen atoms with a corresponding number of deuterium atoms.

In one aspect, the invention provides a method for treating hair loss disorders that can be treated by compounds that modulate (e.g., inhibit) the activity of a JAK (JAK1, JAK2 and/or JAK3). The method comprises administering to a mammalian subject an effective amount of Compound (I), or a pharmaceutically acceptable salt thereof (i.e., an equivalent amount of a pharmaceutically acceptable salt, such as the phosphate salt), once or twice per day, wherein the amount of Compound (I), or a pharmaceutically acceptable salt thereof, is in the range of about 4 mg/day to about 50 mg/day (such as 4 mg/day to 50 mg/day), for example, about 5 mg/day (such as 5 mg/day), about 10 mg/day (such as 10 mg/day), about 20 mg/day (such as 20 mg/day), about 30 mg/day (such as 30 mg/day), about 40 mg/day (such as 40 mg/day), or about 50 mg/day (such as 50 mg/day).

In certain embodiments, the amount of Compound (I), or a pharmaceutically acceptable salt thereof (i.e., an equivalent amount of a pharmaceutically acceptable salt, such as the phosphate salt) administered in the method for treating hair loss disorders, is about 4 mg/day (such as 4 mg/day), about 8 mg/day (such as 8 mg/day), about 16 mg/day (such as 16 mg/day), about 32 mg/day (such as 32 mg/day) or about 48 mg/day (such as 48 mg/day).

In certain embodiments, the amount of Compound (I), or a pharmaceutically acceptable salt thereof administered in the method for treating hair loss disorders, is about 8 mg/day (such as 8 mg/day), about 16 mg/day (such as 16 mg/day), about 24 mg/day (such as 24 mg/day), or about 32 mg/day (such as 32 mg/day). In certain embodiments, the amount of Compound (I), or a pharmaceutically acceptable salt thereof, is about 8 mg/day (such as 8 mg/day), about 12 mg/day (such as 12 mg/day), about 16 mg/day (such as 16 mg/day) or about 24 mg/day (such as 24 mg/day).

In certain embodiments, the amount of Compound (I), or a pharmaceutically acceptable salt thereof administered in the method for treating hair loss disorders, is 10.6 mg/day of Compound (I) phosphate, e.g., administered as a 5.3 mg dose twice daily. In certain embodiments, the amount of Compound (I), or a pharmaceutically acceptable salt thereof, is 21.1 mg/day of Compound (I) phosphate, e.g., administered as a 10.5 mg dose twice daily. In certain embodiments, the amount of Compound (I), or a pharmaceutically acceptable salt thereof, is 31.6 mg/day of Compound (I) phosphate, e.g., administered as a 15.8 mg dose twice daily. In certain embodiments, the amount of Compound (I), or a pharmaceutically acceptable salt thereof, is 42.2 mg/day of Compound (I) phosphate, e.g., administered as a 21.1 mg dose twice daily.

In certain embodiments, the amount of Compound (I), or a pharmaceutically acceptable salt thereof administered in the method for treating hair loss disorders is about 4 mg (such as 4 mg) twice per day. In a specific embodiment, Compound (I) is administered as about 5.3 mg (such as 5.3 mg) of the phosphate salt of Compound (I) twice per day. In certain embodiments, the amount of Compound (I), or a pharmaceutically acceptable salt thereof administered in the method for treating hair loss disorders is about 8 mg (such as 8 mg) twice per day. In a specific embodiment, Compound (I) is administered as about 10.5 mg (such as 10.5 mg) of the phosphate salt of Compound (I) twice per day.

In certain embodiments, the amount of Compound (I), or a pharmaceutically acceptable salt thereof administered in the method for treating hair loss disorders is about 12 mg (such as 12 mg) twice per day. In a specific embodiment, Compound (I) is administered as about 15.8 mg (such as 15.8 mg) of the phosphate salt of Compound (I) twice per day. In certain embodiments, the amount of Compound (I), or a pharmaceutically acceptable salt thereof administered in the method for treating hair loss disorders is about 16 mg (such as 16 mg) twice per day. In a specific embodiment, Compound (I) is administered as about 21.1 mg (such as 21.1 mg) of the phosphate salt of Compound (I) twice per day. In certain embodiments, the hair loss disorder is alopecia areata. In certain embodiments, the subject is a human. In one embodiment, the subject is a human 6 years of age or older. Preferably, Compound (I), or a pharmaceutically acceptable salt thereof (such as the phosphate salt), is administered orally at any of the dosages described herein. Preferably, the Compound (I), or a pharmaceutically acceptable salt thereof, is administered orally at any of the dosages described herein in a pharmaceutical formulation which is a tablet.

In another aspect, the invention provides a method for inducing hair growth in a subject. The method comprises administering to a mammalian subject an effective amount of Compound (I), or a pharmaceutically acceptable salt thereof (i.e., an equivalent amount of a pharmaceutically acceptable salt, such as the phosphate salt), once or twice per day, wherein the amount of Compound (I), or a pharmaceutically acceptable salt thereof, is in the range of about 4 mg/day to about 50 mg/day (such as 4 mg/day to 50 mg/day), for example, about 5 mg/day (such as 5 mg/day), about 10 mg/day (such as 10 mg/day), about 20 mg/day (such as 20 mg/day), about 30 mg/day (such as 30 mg/day), about 40 mg/day (such as 40 mg/day), or about 50 mg/day (such as 50 mg/day).

In certain embodiments, the amount of Compound (I), or a pharmaceutically acceptable salt thereof administered in the method for inducing hair growth, is about 4 mg/day (such as 4 mg/day), about 8 mg/day (such as 8 mg/day), about 16 mg/day (such as 16 mg/day), about 32 mg/day (such as 32 mg/day) or about 48 mg/day (such as 48 mg/day).

In certain embodiments, the amount of Compound (I), or a pharmaceutically acceptable salt thereof administered in the method for inducing hair growth, is about 8 mg/day (such as 8 mg/day), about 16 mg/day (such as 16 mg/day), about 24 mg/day (such as 24 mg/day), or about 32 mg/day (such as 32 mg/day). In certain embodiments, the amount of Compound (I), or a pharmaceutically acceptable salt thereof administered in the method for inducing hair growth, is about 8 mg/day (such as 8 mg/day), about 12 mg/day (such as 12/mg/day), about 16 mg/day (such as 16 mg/day), or about 24 mg/day (such as 24 mg/day).

In certain embodiments, the amount of Compound (I), or a pharmaceutically acceptable salt thereof administered in the method for inducing hair growth, is 10.6 mg/day of Compound (I) phosphate, e.g., administered as a 5.3 mg dose twice daily. In certain embodiments, the amount of Compound (I), or a pharmaceutically acceptable salt thereof, is 21.1 mg/day of Compound (I) phosphate, e.g., administered as a 10.5 mg dose twice daily. In certain embodiments, the amount of Compound (I), or a pharmaceutically acceptable salt thereof, is 31.6 mg/day of Compound (I) phosphate, e.g., administered as a 15.8 mg dose twice daily. In certain embodiments, the amount of Compound (I), or a pharmaceutically acceptable salt thereof, is 42.2 mg/day of Compound (I) phosphate, e.g., administered as a 21.1 mg dose twice daily.

In certain embodiments, the amount of Compound (I), or a pharmaceutically acceptable salt thereof administered in the method for inducing hair growth is about 4 mg (such as 4 mg) twice per day. In a specific embodiment, Compound (I) is administered as about 5.3 mg (such as 5.3 mg) of the phosphate salt of Compound (I) twice per day.

In certain embodiments, the amount of Compound (I), or a pharmaceutically acceptable salt thereof administered in the method for inducing hair growth is about 8 mg (such as 8 mg) twice per day. In a specific embodiment, Compound (I) is administered as about 10.5 mg (such as 10.5 mg) of the phosphate salt of Compound (I) twice per day.

In certain embodiments, the amount of Compound (I), or a pharmaceutically acceptable salt thereof administered in the method for inducing hair growth is about 12 mg (such as 12 mg) twice per day. In a specific embodiment, Compound (I) is administered as the about 15.8 mg (such as 15.8 mg) of the phosphate salt of Compound (I) twice per day.

In certain embodiments, the amount of Compound (I), or a pharmaceutically acceptable salt thereof administered in the method for inducing hair growth is about 16 mg (such as 16 mg) twice per day. In a specific embodiment, Compound (I) is administered as the about 21.1 mg (such as 21.1 mg) of the phosphate salt of Compound (I) twice per day.

In certain embodiments, the subject suffers from a hair loss disorder; in further embodiments, the hair loss disorder is alopecia areata. In certain embodiments, the subject is a human. In one embodiment, the subject is a human 6 years of age or older. Preferably, Compound (I), or a pharmaceutically acceptable salt thereof (such as the phosphate salt), is administered orally at any of the foregoing dosages. Preferably, the Compound (I), or a pharmaceutically acceptable salt thereof, is administered orally at any of the foregoing dosages in a pharmaceutical formulation which is a tablet.

Hair loss disorders include, without limitation, androgenetic alopecia, alopecia areata, telogen effluvium, alopecia totalis, and alopecia universalis.

Alopecia areata is an autoimmune disease that results in partial or complete loss of hair on the scalp and body that may affect up to 650,000 Americans at any given time. The scalp is the most commonly affected area, but any hair-bearing site can be affected alone or together with the scalp. Onset of the disease can occur throughout life and affects both women and men. Alopecia areata can be associated with serious psychological consequences, including anxiety and depression. There are currently no drugs approved by the U.S. Food and Drug Administration (FDA) for the treatment of alopecia areata.

In a specific embodiment, the condition is alopecia areata in a subject such as a mammalian (e.g., human) patient in need thereof. In certain embodiments, the alopecia areata is moderate to severe alopecia areata (for example, hair loss over at least 30% of the scalp, hair loss over at least 40% of the scalp, or hair loss over at least 50% of the scalp).

In one embodiment of any aspect, the compound is administered orally once a day. In other embodiments of any aspect, the compound is administered orally twice per day.

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician.

The administration of Compound (I), or a pharmaceutically acceptable salt thereof (such as the phosphate salt), can continue for as long as necessary to treat a hair loss disorder, e.g., for one week, two weeks, one month, two months, three months, four months, six months, one year, two years, five years, ten years, or longer.

The efficacy of treatment of hair loss disorders such as alopecia areata can be measured in a variety of ways, some of which are known in the art. For example, the "severity of alopecia tool", otherwise known as SALT, is a validated assessment scale—developed by the National Alopecia Areata Foundation working committee—to evaluate the degree of hair loss. See, e.g., Olsen E A, Hordinsky M K, Price V H, et al. Alopecia areata investigational assessment guidelines—Part II. J Am Acad Dermatol 2004: 51: 440-447 (incorporated herein by reference). The SALT score is calculated for a patient by measuring the percentage of hair loss in each of the 4 areas of the scalp and adding the total to achieve a composite score. Hair regrowth is reflected by a decrease in the SALT score. For example, no hair on the scalp would have a SALT score of 100 while complete hair regrowth would be a SALT score of 0. In certain embodiments, methods of treatment as described herein can provide a SALT score improvement of at least 10 points after treatment (for example, from a SALT score of 100 prior to treatment to a SALT score of 90 after treatment). In further embodiments, methods of treatment as described herein can provide a SALT score improvement of at least 20 points, 30 points, 40 points, 50 points, 60 points, 70 points, 80 points, 90 points, or 100 points. In certain embodiments, methods of treatment as described herein can provide after treatment at least a 20% improvement from baseline in the patient's SALT score, or at least a 30% improvement from baseline in the patient's SALT score, or at least a 40% improvement from baseline in the patient's SALT score, or at least a 50% improvement from baseline in the patient's SALT score, or at least a 60% improvement from baseline in the patient's SALT score, or at least a 70% improvement from baseline in the patient's SALT score.

In certain embodiments, treatment is continued for a period of at least four weeks, or at least 8 weeks, or at least 12 weeks, or at least 16 weeks, or at least 20 weeks, or at least 24 weeks, or at least 28 weeks, or at least 32 weeks, or at least 36 weeks, or at least 40 weeks, or at least 44 weeks, or at least 48 weeks, or at least 52 weeks.

In certain embodiments, Compound (I), or a pharmaceutically acceptable salt thereof, is administered in combination with a second therapeutic agent. Preferably, the second therapeutic agent is an agent useful in the treatment of hair loss disorders or autoimmune conditions, such as inhibitors of JAK1, JAK2, or JAK3, and/or STAT1. Such inhibitors include ruxolitinib, tofacitinib, baricitinib, filgotinib, and the like. Other orally administered second therapeutic agents include agents used in the treatment of alopecia areata, including, for example, oral corticosteroids.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000); the FDA-approved labeling information for ruxolitinib and tofacitinib; and clinical trial information for baricitinib and filgotinib, each of which references are incorporated herein by reference in their entirety.

It is expected that some of the second therapeutic agents referenced above will act synergistically with the compounds of this invention. When this occurs, it will allow the effective dosage of the second therapeutic agent and/or Compound (I), or a pharmaceutically acceptable salt thereof, to be reduced from that required in a monotherapy. This has the advantage of minimizing toxic side effects of either the second therapeutic agent or Compound (I), or a pharmaceutically acceptable salt thereof, synergistic improvements in efficacy, improved ease of administration or use and/or reduced overall expense of compound preparation or formulation.

In another embodiment, any of the above methods of treatment comprises the further step of co-administering to the subject in need thereof one or more second therapeutic agents. The choice of second therapeutic agent may be made from any second therapeutic agent known to be useful for treatment of hair loss disorders such as alopecia areata. The choice of second therapeutic agent is also dependent upon the particular disease or condition to be treated. Examples of second therapeutic agents that may be employed in the methods of this invention are those set forth above for use in combination compositions comprising Compound (I), or a pharmaceutically acceptable salt thereof, and a second therapeutic agent. Additional therapeutic agents include agents used in the treatment of alopecia areata, including, for example, topical minoxidil, injected corticosteroids, and anthralin cream or ointment.

The term "co-administered" as used herein means that the second therapeutic agent may be administered together with Compound (I) or a pharmaceutically acceptable salt thereof, as part of a single dosage form (such as a composition of this invention comprising a compound of the invention and an second therapeutic agent as described above) or as separate, multiple dosage forms. Alternatively, the additional agent may be administered prior to, consecutively with, or following the administration of Compound (I), or a pharmaceutically acceptable salt thereof. In such combination therapy treatment, both Compound (I), or a pharmaceutically acceptable salt thereof, and the second therapeutic agent(s) are administered by conventional methods. The administration of a composition of this invention, comprising both Compound (I), or a pharmaceutically acceptable salt thereof, and a second therapeutic agent, to a subject does not preclude the separate administration of that same therapeutic agent, any other second therapeutic agent or Compound (I), or a pharmaceutically acceptable salt thereof, to said subject at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of Compound (I), or a pharmaceutically acceptable salt thereof, is less than its effective amount would be where the second therapeutic agent is not administered. In another embodiment, the effective amount of the second therapeutic agent is less than its effective amount would be where Compound (I), or a pharmaceutically acceptable salt thereof, is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of Compound (I), or a pharmaceutically acceptable salt thereof (i.e., an equivalent amount of a pharmaceutically acceptable salt, such as the phosphate salt), alone or together with one or more of the above-described second therapeutic agents in the manufacture of a medicament, either as a single composition or as separate dosage forms, for treatment or prevention in a subject of a disease, disorder or symptom set forth above. Another aspect of the invention is Compound (I), or a pharmaceutically acceptable salt thereof, for use in the treatment or prevention in a subject of a disease, disorder or symptom thereof delineated herein.

Another aspect of the invention is a pharmaceutical composition comprising Compound (I), in the range of about 4 mg to about 50 mg (for example, about 5 mg, about 10 mg, about 20 mg, about 30 mg, about 40 mg, or about 50 mg), or an equivalent amount of a pharmaceutically acceptable salt thereof, together with a pharmaceutically acceptable carrier or diluent. In certain embodiments, the amount of Compound (I), or a pharmaceutically acceptable salt thereof, is about 4 mg, 8 mg, 16 mg, 24 mg, 32 mg or 48 mg. In certain embodiments, the amount of Compound (I), or a pharmaceutically acceptable salt thereof, is 4 mg, 8 mg, 12 mg, or 16 mg. In certain embodiments, the amount of Compound (I), or a pharmaceutically acceptable salt thereof, is 5.3 mg of Compound (I) phosphate. In certain embodiments, the amount of Compound (I), or a pharmaceutically acceptable salt thereof, is 10.5 or 10.6 mg of Compound (I) phosphate. In certain embodiments, the amount of Compound (I), or a pharmaceutically acceptable salt thereof, is 15.8 mg of Compound (I) phosphate. In certain embodiments, the amount of Compound (I), or a pharmaceutically acceptable salt thereof, is 21.1 mg of Compound (I) phosphate. In certain embodiments, the pharmaceutical composition is a tablet.

Another aspect of the invention is a unit dose form comprising Compound (I), in the range of about 4 mg to about 50 mg (for example, about 5 mg, about 10 mg, about 20 mg, about 30 mg, about 40 mg, or about 50 mg), or an equivalent amount of a pharmaceutically acceptable salt thereof, together with a pharmaceutically acceptable carrier or diluent. In certain embodiments, the amount of Compound (I), or a pharmaceutically acceptable salt thereof, is about 4 mg, 8 mg, 16 mg, 24 mg, 32 mg or 48 mg. In certain embodiments, the amount of Compound (I), or a pharmaceutically acceptable salt thereof, is 4 mg, 8 mg, 12 mg, or 16 mg. In certain embodiments, the amount of Compound (I), or a pharmaceutically acceptable salt thereof, is 5.3 mg of Compound (I) phosphate. In certain embodiments, the amount of Compound (I), or a pharmaceutically acceptable salt thereof, is 10.5 or 10.6 mg of Compound (I) phosphate. In certain embodiments, the amount of Compound (I), or a pharmaceutically acceptable salt thereof, is 15.8 mg of Compound (I) phosphate. In certain embodiments, the amount of Compound (I), or a pharmaceutically acceptable salt thereof, is 21.1 mg of Compound (I) phosphate. In certain embodiments, the unit dose form is a tablet.

In one embodiment, any atom not designated as deuterium is present at its natural isotopic abundance in Compound (I), or a pharmaceutically acceptable salt thereof.

The synthesis of Compound (I), or a pharmaceutically acceptable salt thereof (such as the phosphate salt) may be readily achieved by the methods described U.S. Pat. No. 9,249,149, the teachings of which are incorporated herein by reference, with appropriate modifications. For example, U.S. Pat. No. 9,249,149 describes the use of a D9-intermediate 15 to produce a D9-ruxolitinib product; use of the intermediate A

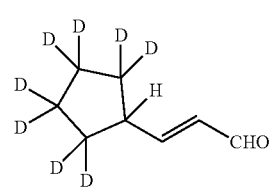

in the methods described in U.S. Pat. No. 9,249,149 furnishes Compound (I). Additionally, intermediate B

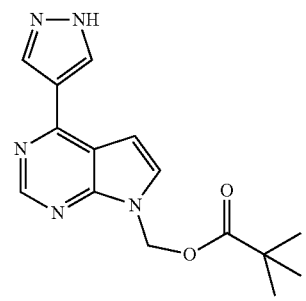

can be used instead of intermediate 14 of U.S. Pat. No. 9,249,149 to prepare Compound (I); removal of the amino protecting group can be accomplished with basic cleavage (e.g., with sodium hydroxide). Phosphoric acid can be used to convert Compound (I) (Free base) to its phosphate salt. Additional methods of preparing ruxolitinib (i.e., non-deuterated Compound (I)) are disclosed in U.S. Pat. No. 9,000, 161, and can be used, with use of suitable deuterated reagents, to prepare Compound (I).

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

The invention also provides pharmaceutical compositions comprising an effective amount of Compound (I), or a pharmaceutically acceptable salt thereof (i.e., an equivalent amount of a pharmaceutically acceptable salt, such as the phosphate salt); and a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament. In certain embodiments, the pharmaceutical composition is provided as a unit dose form.

The invention provides a pharmaceutical composition comprising a pharmaceutically acceptable carrier or diluent and 4 to 50 mg of a compound represented by the following structural formula:

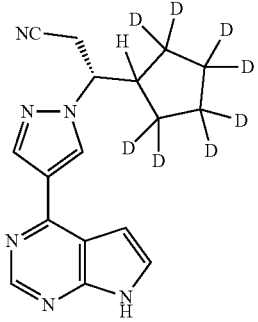

Compound (I)

or a pharmaceutically acceptable salt thereof (i.e., an equivalent amount of a pharmaceutically acceptable salt, such as the phosphate salt).

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral administration. Other formulations may conveniently be presented in unit dosage form, e.g., tablets, sustained release capsules, granules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption. In a specific embodiment, the compound is administered orally as a tablet.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added. In another embodiment, the composition is in the form of a tablet. In certain embodiments, exemplary formulations for the tablet are disclosed in U.S. Pat. No. 8,754,224, the teachings of which are herein incorporated by reference.

In a particular embodiment, a tablet formulation contains about 4 mg to about 50 mg of Compound (I), or an equivalent amount of a pharmaceutically acceptable salt thereof (such as the phosphate salt), and the following inactive ingredients: colloidal silicon dioxide, magnesium stearate, microcrystalline cellulose, and povidone. Wet granulation followed by compression provides tablets comprising Compound (I), or a pharmaceutically acceptable salt thereof. For example, to prepare a 200 mg tablet comprising the equivalent of 16 mg of Compound (I), 10.6 wt % of Compound (I) phosphate and 64.44 wt % Avicel PH-101 microcrystalline cellulose are mixed in a higher shear granulator, and an 8.5% w/w aqueous Kollidon 30 solution (containing Kollidon 30, a polyvinylpyrrolidone (povidone); 5 wt % (based on the total formulation weight) is added during mixing to form granules. The granules are tray-dried in an oven at 60±10° C. and milled using a Quadro Comil U5 mill. The granules retained on the comil screen are forced through a #20 mesh sieve using a stainless steel spatula. The resulting milled granules are mixed with Avicel PH-200 microcrystalline cellulose (18.5 wt %), Aerosil 200 colloidal silicon dioxide (0.5 wt %) and Hyqual magnesium stearate (1 wt %) in a Turbula mixer to form the final blend. The final blend is compressed into 200 mg tablets using a Riva Piccola rotary press tooled with 0.451"×0.229" D-type modified capsule shape tooling. Each tablet contains 21.1 mg Compound (I) (equivalent to 16 mg of Compound (I) free base).

In a particular embodiment, the tablet contains about 10.5 mg or about 10.6 mg of the phosphate salt of Compound (I) (equivalent to 8 mg of Compound (I) free base).

In a particular embodiment, the tablet comprises the following ingredients:

4 mg Tablet

| Component | Function | Wt % | Amount per unit (mg) |
|---|---|---|---|
| Compound (I) Phosphate | Active | 2.6 | 5.3* |
| Microcrystalline Cellulose | Diluent/Binder | 90.9 | 181.7 |
| Povidone | Binder | 5.0 | 10.0 |

-continued

| Component | Function | Wt % | Amount per unit (mg) |
|---|---|---|---|
| Colloidal Silicon Dioxide | Glidant | 0.5 | 1.0 |
| Magnesium Stearate | Lubricant | 1.0 | 2.0 |
| Purified Water | Solvent | Removed during processing | |
| Total | | 100.0 | 200.0 |

*Equivalent to 4 mg Compound (I) free base

In another particular embodiment, the tablet comprises the following ingredients:
8 mg Tablet

| Component | Function | Wt % | Amount per unit (mg) |
|---|---|---|---|
| Compound (I) Phosphate | Active | 5.2 | 10.5* |
| Microcrystalline Cellulose | Diluent/Binder | 90.8 | 181.5 |
| Povidone | Binder | 2.5 | 5.0 |
| Colloidal Silicon Dioxide | Glidant | 0.5 | 1.0 |
| Magnesium Stearate | Lubricant | 1.0 | 2.0 |
| Purified Water | Solvent | Removed during processing | |
| Total | | 100.0 | 200.0 |

*Equivalent to 8 mg Compound (I) free base

In an alternative particular embodiment, the tablet comprises the following ingredients:
8 mg Tablet

| Component | Function | Wt % | Amount per unit (mg) |
|---|---|---|---|
| Compound (I) Phosphate | Active | 5.3 | 10.6* |
| Microcrystalline Cellulose | Diluent/Binder | 88.2 | 176.4 |
| Povidone | Binder | 5.0 | 10.0 |
| Colloidal Silicon Dioxide | Glidant | 0.5 | 1.0 |
| Magnesium Stearate | Lubricant | 1.0 | 2.0 |
| Purified Water | Solvent | Removed during processing | |
| Total | | 100.0 | 200.0 |

*Equivalent to 8 mg Compound (I) free base

In still another particular embodiment, the tablet comprises the following ingredients:
16 mg Tablet

| Component | Function | Wt % | Amount per unit (mg) |
|---|---|---|---|
| Compound (I) Phosphate | Active | 10.6 | 21.1* |
| Microcrystalline Cellulose | Diluent/Binder | 82.9 | 165.9 |
| Povidone | Binder | 5.0 | 10.0 |
| Colloidal Silicon Dioxide | Glidant | 0.5 | 1.0 |
| Magnesium Stearate | Lubricant | 1.0 | 2.0 |
| Purified Water | Solvent | Removed during processing | |
| Total | | 100.0 | 200.0 |

*Equivalent to 16 mg Compound (I) free base

In another embodiment, a composition of this invention further comprises a second therapeutic agent. The second therapeutic agent may be selected from any compound or therapeutic agent known to have or that demonstrates advantageous properties when administered with a compound having the same mechanism of action as ruxolitinib.

Preferably, the second therapeutic agent is an agent useful in the treatment of hair loss disorders or autoimmune conditions, including inhibitors of JAK1, JAK2, or JAK3, and/or STAT1. Such inhibitors include ruxolitinib, tofacitinib, baricitinib, filgotinib, and the like. Other second therapeutic agents include oral corticosteroids.

In another embodiment, the invention provides separate dosage forms of Compound (I), or a pharmaceutically acceptable salt thereof, and one or more of any of the above-described second therapeutic agents, wherein Compound (I), or a pharmaceutically acceptable salt thereof, and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, Compound (I), or a pharmaceutically acceptable salt thereof, is present in an effective amount. As used herein, the term "effective amount" refers to an amount which, when administered in a proper dosing regimen, is sufficient to treat the target disorder.

The interrelationship of dosages for animals and humans (based on milligrams per meter squared of body surface) is described in Freireich et al., Cancer Chemother. Rep, 1966, 50: 219. Body surface area may be approximately determined from height and weight of the subject. See, e.g., Scientific Tables, Geigy Pharmaceuticals, Ardsley, N.Y., 1970, 537.

In one embodiment, an effective amount of Compound (I) (either as the free base, or as an equivalent amount of a pharmaceutically acceptable salt, such as the phosphate salt) can range from about 4 mg to 50 mg per day (such as 4 mg to 50 mg per day), such as, about 5 mg/day (such as 5 mg/day), about 10 mg/day (such as 10 mg/day), about 20 mg/day (such as 20 mg/day), about 30 mg/day (such as 30 mg/day), about 40 mg/day (such as 40 mg/day), or about 50 mg/day (such as 50 mg/day). In certain embodiments, the amount is about 4 mg/day (such as 4 mg/day), about 8 mg/day (such as 8 mg/day), about 16 mg/day (such as 16 mg/day), about 24 mg/day (such as 24 mg/day), about 32 mg/day (such as 32 mg/day) or about 48 mg/day (such as 48 mg/day). In one embodiment, a dose of about 4 mg/day (such as 4 mg/day), about 8 mg/day (such as 8 mg/day), about 16 mg/day (such as 16 mg/day), about 24 mg/day (such as 24 mg/day), about 32 mg/day (such as 32 mg/day) or about 48 mg/day (such as 48 mg/day) is administered once a day. In a specific example, a dose of 16 mg/day is administered as two 8 mg tablets of Compound (I) (either as the free base, or as an equivalent amount of a pharmaceutically acceptable salt, such as the phosphate salt) administered together (i.e., as a single dose). In another specific example, a dose of 16 mg/day is administered as one 16 mg tablet of Compound (I) (either as the free base, or as an equivalent amount of a pharmaceutically acceptable salt, such as the phosphate salt). In another embodiment, a dose of 4 mg/day, 8 mg/day, 16 mg/day, 24 mg/day, 32 mg/day or 48 mg/day is administered in divided doses, twice a day (e.g., a 48 mg/day dose is administered as 24 mg twice daily). In another embodiment, a dose of 8 mg/day, 16 mg/day, 24 mg/day, or 32 mg/day is administered in divided doses, twice a day (e.g., a 32 mg/day dose is administered as 16 mg of Compound (I) (either as the free base, or as an equivalent amount of a pharmaceutically acceptable salt, such as the phosphate salt) twice daily, i.e., in separate doses. In one specific embodiment, a dose of 16 mg/day is administered as 8 mg of Compound (I) (either as the free base, or as an equivalent amount of a pharmaceutically acceptable salt, such as the phosphate salt) twice daily, i.e., in separate doses. It will be understood that reference to an amount of Compound (I), or a pharmaceutically acceptable salt thereof, includes an amount of a pharmaceutically acceptable salt of Compound (I) (such as the phosphate salt) which is equivalent to the stated amount of Compound (I) as the free base (e.g., 10.5 mg of Compound (I) phosphate salt is equivalent to 8 mg of Compound (I) free base).

In certain embodiments, an effective amount of Compound (I), or a pharmaceutically acceptable salt thereof is about 4 mg (such as 4 mg) twice per day. In a specific embodiment, an effective amount of Compound (I) is administered as about 5.3 mg (such as 5.3 mg) of the phosphate salt of Compound (I) twice per day. In certain embodiments, an effective amount of Compound (I), or a pharmaceutically acceptable salt thereof is about 8 mg (such as 8 mg) twice per day. In a specific embodiment, Compound (I) is administered as about 10.5 mg (such as 10.5 mg) of the phosphate salt of Compound (I) twice per day.

In certain embodiments, an effective amount of Compound (I), or a pharmaceutically acceptable salt thereof is about 12 mg (such as 12 mg) twice per day. In a specific embodiment, effective amount of Compound (I) is about 15.8 mg (such as 15.8 mg) of the phosphate salt of Compound (I) twice per day. In certain embodiments, an effective amount of Compound (I), or a pharmaceutically acceptable salt thereof is about 16 mg (such as 16 mg) twice per day. In a specific embodiment, the effective amount of Compound (I) is about 21.1 mg (such as 21.1 mg) of the phosphate salt of Compound (I) twice per day.

EXAMPLES

Example 1. Determination of Metabolic Stability of D-Ruxolitinib Using

CYP3A4 Supersomes

Materials and Methods:

Materials: CYP3A4 supersomes were obtained from Corning Gentest. (β-nicotinamide adenine dinucleotide phosphate, reduced form (NADPH), magnesium chloride ($MgCl_2$), and dimethyl sulfoxide (DMSO) were purchased from Sigma-Aldrich. Deuterated test compounds were supplied by Concert Pharmaceuticals.

Determination of Metabolic Stability: 10 mM stock solutions of test compounds were prepared in DMSO. The 7.5 mM stock solutions were diluted to 12.75 µM in acetonitrile (ACN). The CYP3A4 supersomes were diluted in 0.1 M potassium phosphate buffer, pH 7.4, containing 3 mM $MgCl_2$. The diluted supersomes were added to wells of a 96-well deep-well polypropylene plate in triplicate. A 10 µL aliquot of the 12.75 µM test compound was added to the supersomes and the mixture was pre-warmed for 10 minutes. Reactions were initiated by addition of pre-warmed NADPH solution. The final reaction volume was 0.5 mL and contained 50 pmol/mL CYP3A4 supersomes, 0.25 µM test compound, and 2 mM NADPH in 0.1 M potassium phosphate buffer, pH 7.4, and 3 mM $MgCl_2$. The reaction mixtures were incubated at 37° C. and 50 µL aliquots were removed at 0, 5, 10, 20, and 30 minutes and added to shallow-well 96-well plates which contained 50 µL of ice-cold ACN with internal standard to stop the reactions. The plates were stored at 4° C. for 20 minutes after which 100 µL of water was added to the wells of the plate before centrifugation to pellet precipitated proteins. Supernatants were transferred to another 96-well plate and analyzed for amounts of parent remaining by LC-MS/MS using an Applied Bio-systems mass spectrometer.

Data analysis: The in vitro $t_{1/2}$s for test compounds were calculated from the slopes of the linear regression of % parent remaining (ln) vs incubation time relationship.

in vitro $t_{1/2} = 0.693/k$ k=−[slope of linear regression of % parent remaining(ln) vs incubation time]

Data analysis was performed using Microsoft Excel Software.

It was found that Compound (I) had a $t_{1/2}$ about 80% longer than the $t_{1/2}$ of non-deuterated ruxolitinib. These results show that Compound (I) is substantially more stable metabolically than ruxolitinib in the CYP3A4 supersome assay.

Example 2. Determination of Metabolic Stability of D-Ruxolitinib Using Human Liver Microsomes Materials:

Human liver microsomes (20 mg/mL) were obtained from Xenotech, LLC (Lenexa, Kans.). β-nicotinamide adenine dinucleotide phosphate, reduced form (NADPH), magnesium chloride ($MgCl_2$), and dimethyl sulfoxide (DMSO) were purchased from Sigma-Aldrich. Deuterated test compounds were supplied by Concert Pharmaceuticals.

Determination of Metabolic Stability:

7.5 mM stock solutions of test compounds were prepared in DMSO. The 7.5 mM stock solutions were diluted to 12.5 µM in acetonitrile (ACN). The human liver microsomes were diluted in 0.1 M potassium phosphate buffer, pH 7.4, containing 3 mM $MgCl_2$. The diluted microsomes were added to wells of a 96-well deep-well polypropylene plate in triplicate. A 10 µL aliquot of the 12.5 µM test compound was added to the microsomes and the mixture was pre-warmed for 10 minutes. Reactions were initiated by addition of pre-warmed NADPH solution. The final reaction volume was 0.5 mL and contained 5 mg/mL human liver microsomes, 0.25 µM test compound, and 2 mM NADPH in 0.1 M potassium phosphate buffer, pH 7.4, and 3 mM $MgCl_2$. The reaction mixtures were incubated at 37° C., and 50 µL aliquots were removed at 0, 5, 10, 20, and 30 minutes and added to shallow-well 96-well plates which contained 50 µL of ice-cold ACN with internal standard to stop the reactions. The plates were stored at 4° C. for 20 minutes after which 100 µL of water was added to the wells of the plate before centrifugation to pellet precipitated proteins. Supernatants were transferred to another 96-well plate and analyzed for amounts of parent remaining by LC-MS/MS using an Applied Bio-systems mass spectrometer.

Data Analysis:

The in vitro $t_{1/2}$s for test compounds were calculated from the slopes of the linear regression of % parent remaining (ln) vs incubation time relationship.

in vitro $t_{1/2} = 0.693/k$ k=−[slope of linear regression of % parent remaining(ln) vs incubation time]

Data analysis was performed using Microsoft Excel Software.

It was found that Compound (I) had a $t_{1/2}$ about 75% longer than the $t_{1/2}$ of non-deuterated ruxolitinib. These results show that Compound (I) is substantially more stable metabolically than ruxolitinib in the HLM assay.

Example 3—Human Studies

Figure 1B:
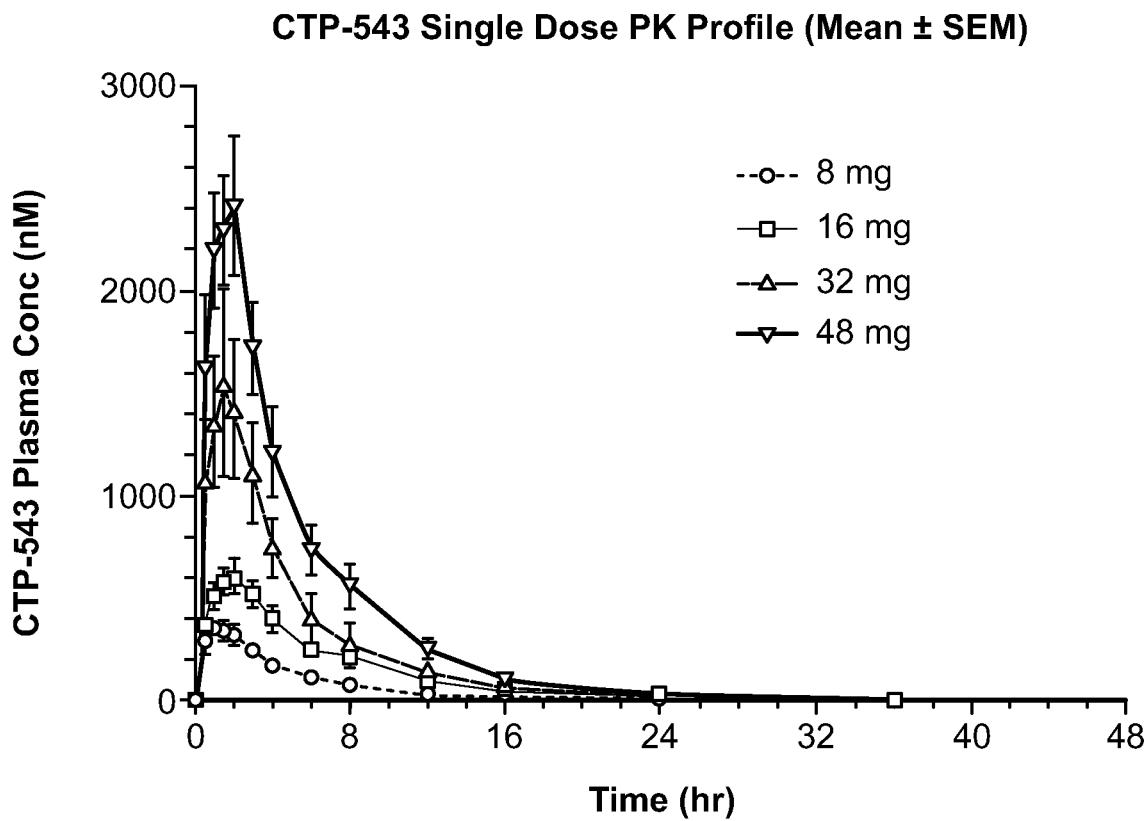
FIG. 1B is a graph showing plasma concentration of CTP-543 (Compound (I)) from 0-48 hours after dosing.

Single Ascending Dose (SAD) Study: Healthy volunteers were administered doses of Compound (I) or placebo under fasted conditions. The objective of the study was to evaluate the pharmacokinetics of a single dose of 8 mg, 16 mg, 32 mg, or 48 mg of Compound (I) as the phosphate salt (e.g., 10.5 mg of Compound (I) phosphate salt is equivalent to 8 mg of Compound (I) free base). For each dose group, 6 subjects received Compound (I), and 2 subjects received placebo. The study design is shown in FIG. 1A. Metabolites of Compound (I) were analyzed. Doses of Compound (I) were administered as Compound (I) phosphate salt as a powder-in-capsule, administered with water. The preliminary results are shown in FIGS. 1B and 1C.

Multiple Ascending Dose Study: Healthy volunteers were administered doses of Compound (I) or placebo under fasted conditions. The objective of the study was to evaluate the pharmacokinetics of daily administration of 8 mg, 16 mg, 24 mg, or 32 mg of Compound (I) as the phosphate salt (e.g., 10.5 mg of Compound (I) phosphate salt is equivalent to 8 mg of Compound (I) free base). Compound (I) was administered once per day (QD) (8 mg, 24 mg, 32 mg doses) or twice per day (BID) (two 8 mg doses totaling 16 mg/day, or two 16 mg doses totaling 32 mg/day) for seven consecutive days. For each dose group, 8 subjects received Compound (I), and 2 subjects received placebo. The study design is shown in FIG. 1A. Metabolites of Compound (I) were analyzed. Doses of Compound (I) were administered as 8 mg tablets, with water. The preliminary results are shown in FIGS. 1B and 1C.

Final results are shown in the following table:

| Treatment | Median (range) $T_{max}$ (hr) | Arithmetic Mean (CV %) | | | | | | |
|---|---|---|---|---|---|---|---|---|
| | | $C_{max}$ (ng/mL) | $t_{1/2}$ (hr) | $AUC_{0-24hr}$ (hr * ng/mL) | $AUC_{0-inf}$ (hr * ng/mL) | $C_{24hr}$ (ng/mL) | CL/F (L/hr) | Vz/F (L) |
| CTP-543 8 mg (n = 6) | 1.25 (0.50-1.50) | 118 (28.4%) | 3.14 (28.4%) | 584 (31.3%) | 589 (31.6%) | 1.02 (94.9%) | 14.92 (34.9%) | 64.1 (27.8%) |
| CTP-543 16 mg (n = 6) | 1.50 (0.50-3.20) | 260 (39.2%) | 3.32 (25.9%) | 1329 (34.7%) | 1347 (35.2%) | 2.77 (78.4%) | 13.87 (52.4%) | 61.0 (28.0%) |
| CTP-543 32 mg (n = 6) | 1.25 (0.50-2.00) | 535 (29.0%) | 3.52 (15.9%) | 2424 (25.2%) | 2462 (26.3%) | 5.60 (104.5%) | 13.88 (30.2%) | 68.4 (21.3%) |
| CTP-543 48 mg (n = 5) | 1.50 (0.50-2.00) | 853 (25.7%) | 3.61 (21.4%) | 4095 (34.2%) | 4159 (35.1%) | 9.26 (80.1%) | 12.75 (34.1%) | 63.2 (25.6%) |

Figure 2A:
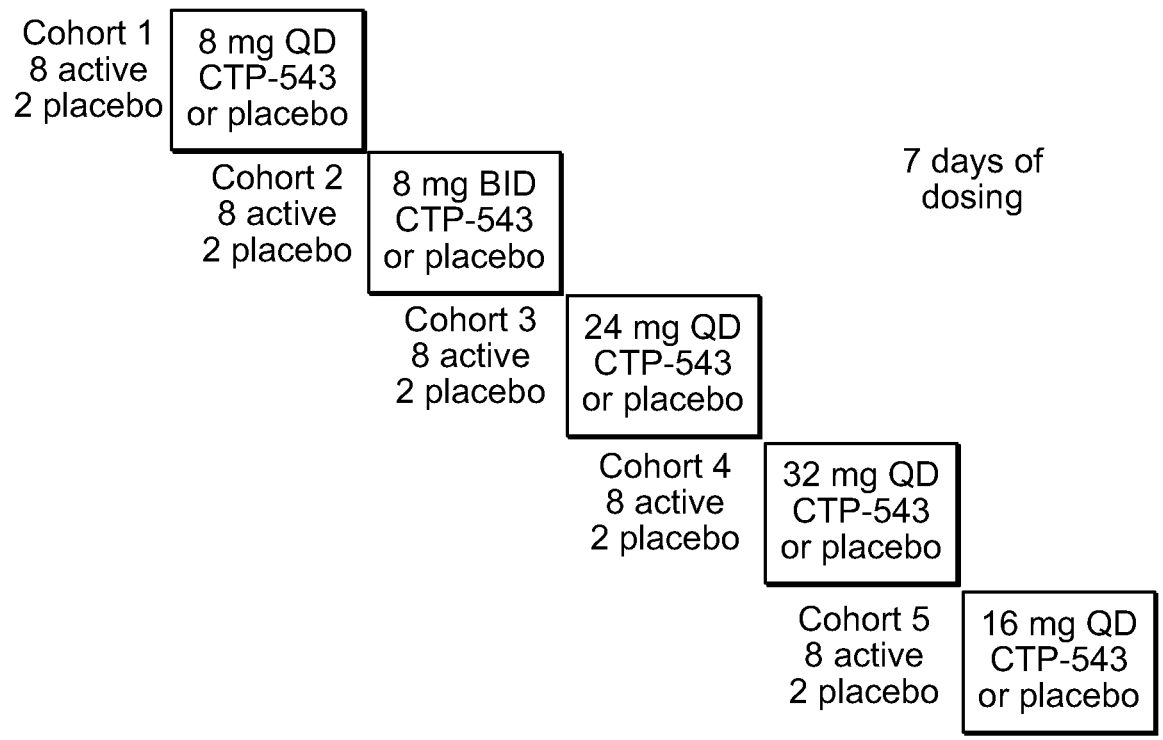
FIG. 2A depicts a study design for a multiple ascending dose (MAD) trial in healthy volunteers.
Figure 2B:
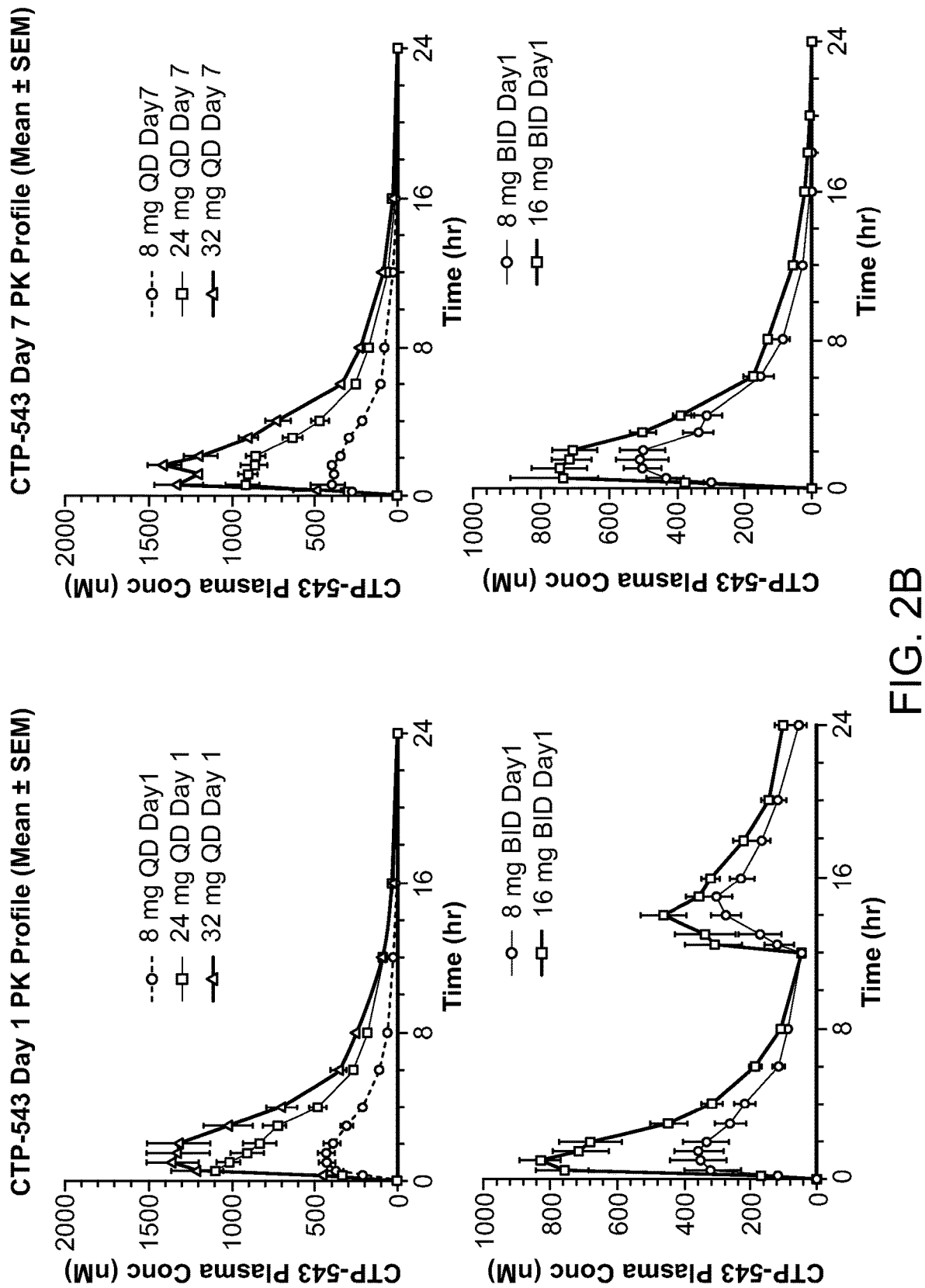
FIG. 2B is a graph showing plasma concentration of CTP-543 (Compound (I)) from 0-24 hours on Day 1 and Day 7 of the MAD study.

Preliminary results from the SAD study are shown in FIGS. 1B and 1C. Preliminary results from the MAD study are shown in FIGS. 2B and 2C. Final results from the MAD study are shown in the following tables. In FIGS. 1 and 2, CTP-543 is Compound (I), administered as the phosphate salt.

| Dose Level of CTP-543 | Study Day | Median (range) $T_{max}$ (hr) | Arithmetic Mean (CV %) | | | |
|---|---|---|---|---|---|---|
| | | | $C_{max}$ (ng/mL) | $AUCtau/AUC_{0-24hr}$ (hr * ng/mL) | $C_{24hr}$ (ng/mL) | $t_{1/2}$ (hr) |
| 8 mg QD (n = 7) | Day 1 | 1.00 (0.50-2.00) | 156 (31.2%) | 704 (26.4%) | 0.86 (45.3%) | 3.23 (9.6%) |
| | Day 7 | 1.00 (0.25-1.50) | 151 (34.1%) | 668 (27.8%) | 1.01 (75.0%) | 3.51 (20.9%) |
| 24 mg QD (n = 8) | Day 1 | 0.50 (0.25-2.00) | 384 (22.2%) | 1672 (25.7%) | 2.48 (134%) | 3.14 (28.8%) |
| | Day 7 | 1.00 (0.50-2.00) | 310 (22.9%) | 1534 (25.2%) | 3.39 (160%) | 3.50 (25.2%) |
| 32 mg QD (n = 8) | Day 1 | 0.75 (0.50-2.00) | 509 (32.8%) | 2219 (36.2%) | 2.95 (141%) | 2.86 (32.1%) |
| | Day 7 | 0.75 (0.50-2.00) | 492 (18.0%) | 2104 (27.8%) | 5.12 (153%) | 3.45 (37.1%) |

| Dose Level of CTP-543 | Study Day | Median (range) $T_{max}$ (hr) | Arithmetic Mean (CV %) | | | |
|---|---|---|---|---|---|---|
| | | | $C_{max}$ (ng/mL) | $AUCtau/AUC_{0-12hr}$ (hr * ng/mL) | $C_{12hr}$ (ng/mL) | $t_{1/2}$ (hr) |
| 8 mg BID (n = 4) | Day 1 | 1.00 (0.50-1.50) | 160 (17.5%) | 703 (24.5%) | 13.7 (55.9%) | 3.77 (23.4%) |
| | Day 7 | 1.50 (0.25-2.00) | 183 (25.7%) | 844 (39.8%) | 13.2 (59.6%) | 4.20 (32.3%) |

-continued

| Dose Level of CTP-543 | Study Day | Median (range) T$_{max}$ (hr) | Arithmetic Mean (CV %) | | | |
|---|---|---|---|---|---|---|
| | | | C$_{max}$ (ng/mL) | AUCtau/AUC$_{0-12hr}$ (hr * ng/mL) | C$_{12hr}$ (ng/mL) | t$_{1/2}$ (hr) |
| 16 mg BID (n = 8) | Day 1 | 1.00 (0.50-2.00) | 290 (19.7%) | 1062 (22.5%) | 15.3 (53.9%) | 2.89 (31.4%) |
| | Day 7 | 0.75 (0.50-2.00) | 288 (36.3%) | 1127 (26.6%) | 16.5 (71.6%) | 3.53 (19.3%) |

In the combined SAD and MAD studies, a total of 77 subjects were dosed (60 received CTP-543; 17 received placebo). CTP-543 was rapidly absorbed and did not accumulate with repeated dosing. No serious adverse events were reported; the most common adverse event reported was headache. No withdrawal or dose modification related to CTP-543 occurred. Cases of mild neutropenia resolved or trended toward recovery after dosing completion. Severe neutropenia (Grade 3 or 4) was not observed.

In the Phase 1 study, Compound (I) was generally well tolerated. Based on these studies, doses of 8 mg BID (twice daily), 12 mg BID, 16 mg BID and 32 mg BID were selected.

Additional findings from the Phase 1 study show that the average systemic exposure of 16 mg BID of Compound (I), the highest dose being evaluated in the Phase 2a trial described below, appears comparable to published findings for average reported exposure of the 20 mg BID ruxolitinib dose shown to be effective at inducing hair regrowth in patients with moderate to severe alopecia. (See, e.g., *JCI Insight.* 2016; 1(15):e89790. doi:10.1172/jci.insight.89790.)

Pharmacodynamic analyses were also performed during the MAD study of the Phase 1 trial to assess the inhibition of IL-6- and IFN-γ-mediated JAK/STAT signaling. Consistent with the established pharmacological activity of CTP-543 (Compound (I)), a dose-related reduction in IL-6-stimulated phosphorylated STAT3 (pSTAT3) was observed. In general, pSTAT3 inhibition in all treatment groups returned to approximate baseline values at 24 hours postdose. Also, IFN-γ-mediated STAT1 signaling, which is believed to play a key role in the pathogenesis of alopecia areata, was significantly inhibited in disease-relevant immune cell types at all doses evaluated.

A Phase 2a trial has been designed to evaluate the safety and efficacy of Compound (I) after 12 months of dosing with the primary efficacy analysis at week 24. The Phase 2a trial is a double-blind, randomized, placebo-controlled, parallel dose trial to evaluate the safety and efficacy of Compound (I) in adult patients with moderate-to-severe alopecia areata. Approximately 100 patients will be randomized to receive one of four doses of Compound I as the phosphate salt (e.g., 10.5 mg of Compound (I) phosphate salt is equivalent to 8 mg of Compound (I) free base). The four doses of Compound (I) are 4, 8 (i.e., about 10.5 mg of Compound (I) phosphate salt), 12 and 16 mg twice daily, and there is also a patient group receiving placebo. The primary outcome measure will utilize the severity of alopecia tool (SALT) after 24 weeks of dosing. The trial will include an additional 28 weeks of dosing where all patients enrolled in the study will receive Compound (I).

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

What is claimed is:

1. A method of treating a hair loss disorder in a human subject, the method comprising administering to the human subject 16 mg/day of a compound represented by the following structural formula:

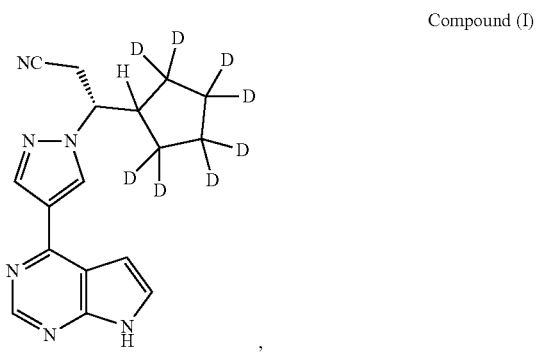 [SMILES: [2H]C1([2H])C([C@@H](CC#N)n2cc(-c3ncnc4[nH]ccc34)cn2)C([2H])([2H])C([2H])([2H])C1([2H])[2H]]

Compound (I)

or a pharmaceutically acceptable salt thereof, wherein each position in Compound (I) designated specifically as deuterium has at least 95% incorporation of deuterium.

2. The method of claim 1, wherein the hair loss disorder is alopecia areata.

3. The method of claim 1, wherein the compound is administered orally.

4. The method of claim 1, wherein the compound is administered in a pharmaceutical formulation which is a tablet.

5. The method of claim 1, wherein the compound is administered once a day.

6. The method of claim 1, wherein the compound is administered twice a day.

7. The method of claim 6, wherein the step of administering comprises administering to the subject 8 mg of the compound twice per day.

8. The method of claim 1, wherein the incorporation of deuterium at each position designated specifically as deuterium is at least 97%.

9. The method of claim 1, wherein the compound is orally administered as a phosphate salt.

10. The method of claim 9, wherein the phosphate salt is administered once a day.

11. The method of claim 9, wherein the phosphate salt is administered twice a day.

12. The method of claim 8, wherein the compound is orally administered as a phosphate salt.

13. The method of claim 12, wherein the phosphate salt is administered once a day.

14. The method of claim 12, wherein the phosphate salt is administered twice a day.

15. The method of claim 2, wherein the compound is administered orally.

16. The method of claim 2, wherein the compound is administered in a pharmaceutical formulation which is a tablet.

17. The method of claim 2, wherein the compound is administered once a day.

18. The method of claim 2, wherein the compound is administered twice a day.

19. The method of claim 18, wherein the step of administering comprises administering to the subject 8 mg of the compound twice per day.

20. The method of claim 2, wherein the incorporation of deuterium at each position designated specifically as deuterium is at least 97%.

21. The method of claim 2, wherein the compound is orally administered as a phosphate salt.

22. The method of claim 21, wherein the phosphate salt is administered once a day.

23. The method of claim 21, wherein the phosphate salt is administered twice a day.

24. The method of claim 20, wherein the compound is orally administered as a phosphate salt.

25. The method of claim 24, wherein the phosphate salt is administered once a day.

26. The method of claim 24, wherein the phosphate salt is administered twice a day.

27. A method of treating alopecia areata in a human subject, the method comprising orally administering to the human subject 8 mg twice per day of a compound represented by the following structural formula:

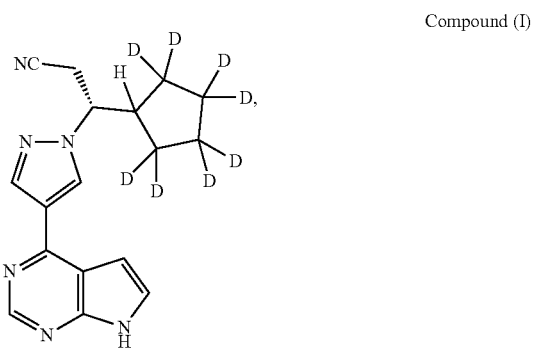

Compound (I)

wherein Compound (I) is administered as a phosphate salt, and wherein each position in Compound (I) designated specifically as deuterium has at least 95% incorporation of deuterium.

28. The method of claim 27, wherein the incorporation of deuterium at each position designated specifically as deuterium is at least 97%.

29. The method of claim 28, wherein the Compound (I) is administered in a tablet.

* * * * *